(12) United States Patent
Goodwin et al.

(10) Patent No.: US 10,078,269 B2
(45) Date of Patent: Sep. 18, 2018

(54) ARRAY OF ENCODERS FOR ALIGNMENT MEASUREMENT

(71) Applicant: NIKON CORPORATION, Tokyo (JP)

(72) Inventors: Eric Peter Goodwin, Oro Valley, AZ (US); Michael B. Binnard, Belmont, CA (US); Ruslan Kurdyumov, San Francisco, CA (US)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/283,669

(22) Filed: Oct. 3, 2016

(65) Prior Publication Data
US 2017/0097574 A1  Apr. 6, 2017

Related U.S. Application Data

(60) Provisional application No. 62/236,275, filed on Oct. 2, 2015.

(51) Int. Cl.
*G03B 27/52* (2006.01)
*G03B 27/54* (2006.01)
(Continued)

(52) U.S. Cl.
CPC ........ *G03F 7/70141* (2013.01); *G01J 1/0414* (2013.01); *G01J 1/0448* (2013.01);
(Continued)

(58) Field of Classification Search
CPC .. G01D 5/2455; G01D 5/2457; G01D 5/3473; G01D 5/38; G01D 5/34746;
(Continued)

(56) References Cited

U.S. PATENT DOCUMENTS

| 6,034,378 A | 3/2000 | Shiraishi |
| 7,023,610 B2 | 4/2006 | Ohtsuki et al. |

(Continued)

FOREIGN PATENT DOCUMENTS

| WO | 2012041457 A2 | 4/2012 |
| WO | 2012177663 A2 | 12/2012 |

*Primary Examiner* — Mesfin Asfaw
(74) *Attorney, Agent, or Firm* — Yakov S. Sidorin; Quarles & Brady LLP

(57) ABSTRACT

System and method for accurately measuring alignment of every exposure field on a pre-patterned wafer without reducing wafer-exposure throughput. Diffraction grating disposed in scribe-lines of such wafer, used as alignment marks, and array of encoder-heads (each of which is configured to define positional phase(s) of at least one such alignment mark) are used. Determination of trajectory of a wafer-stage scanning during the wafer-exposure in the exposure tool employs determining in-plane coordinates of such spatially-periodic alignment marks by simultaneously measuring position-dependent phases of signals produced by these marks as a result of recombination of light corresponding to different diffraction orders produced by these marks. Measurements may be performed simultaneously at all areas corresponding to at least most of the exposure fields of the wafer, and/or with use of a homodyne light source, and/or in a wavelength-independent fashion, and/or with a pre-registration process allowing for accommodation of wafers with differently-dimensioned exposure fields.

45 Claims, 19 Drawing Sheets

(51) Int. Cl.
*G03F 7/20* (2006.01)
*G01J 1/04* (2006.01)
*G01N 21/47* (2006.01)

(52) U.S. Cl.
CPC ........ *G01J 1/0477* (2013.01); *G01N 21/4788* (2013.01); *G01N 21/4795* (2013.01)

(58) Field of Classification Search
CPC .. G01D 11/245; G01D 5/24438; G01D 5/345; G01D 5/2415; G01D 5/2458; F16C 41/007
See application file for complete search history.

(56) References Cited

U.S. PATENT DOCUMENTS

| | | |
|---|---|---|
| 7,897,942 B1 | 3/2011 | Bareket et al. |
| 8,570,487 B2 | 10/2013 | Khuat Duy et al. |
| 8,610,898 B2 | 12/2013 | Khuat Duy |
| 8,829,420 B2 | 9/2014 | Goodwin et al. |
| 9,243,896 B2 | 1/2016 | Goodwin |
| 9,360,347 B2 | 6/2016 | Goodwin et al. |
| 2007/0296973 A1* | 12/2007 | Kiers ................... G01N 21/21 356/369 |
| 2012/0057171 A1* | 3/2012 | Khuat Duy ............ G02B 27/40 356/494 |
| 2013/0128255 A1 | 5/2013 | Liu |
| 2014/0049762 A1 | 2/2014 | Goodwin |
| 2015/0276385 A1 | 10/2015 | Goodwin et al. |
| 2015/0286613 A1 | 10/2015 | Boyle et al. |
| 2016/0026129 A1 | 1/2016 | Tanaka |

\* cited by examiner

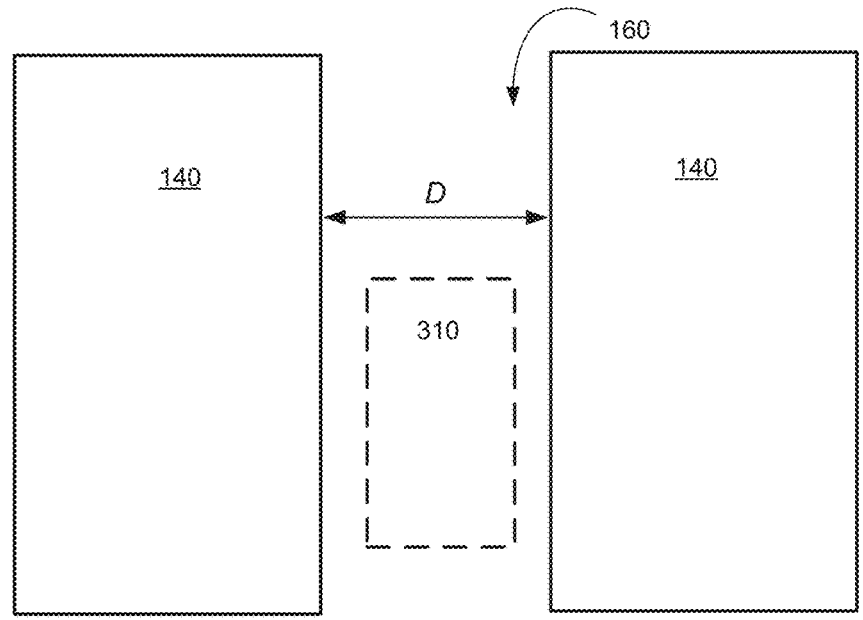
FIG. 3A
FIG. 3B
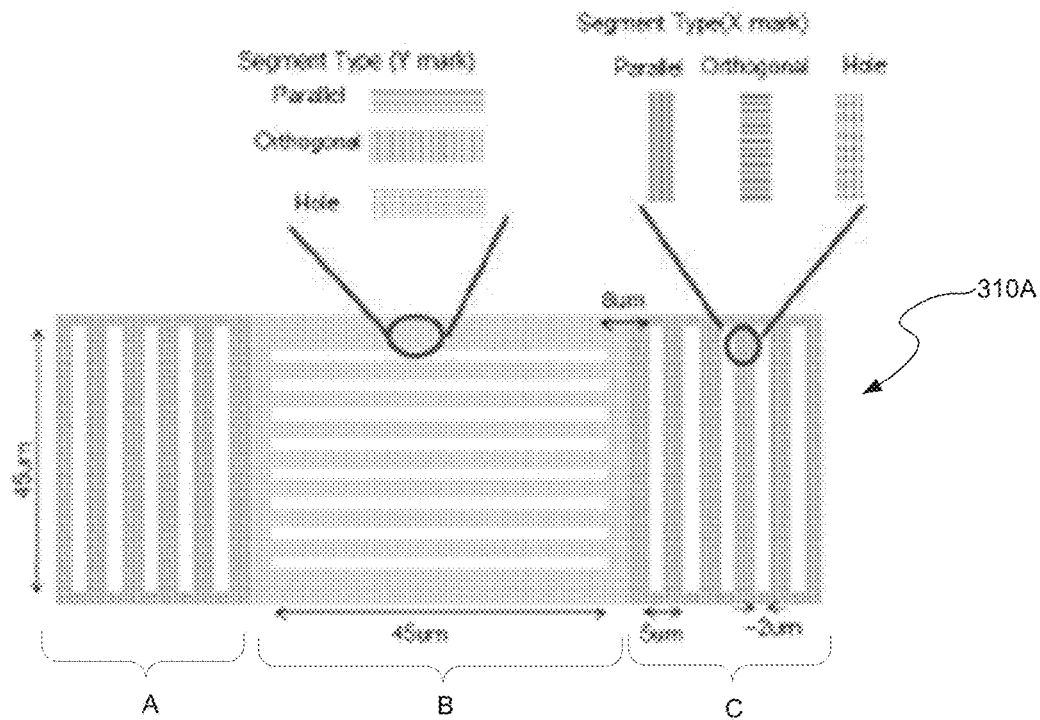

Top view of 400

Projection lens not shown

ARRAY OF ENCODERS FOR ALIGNMENT MEASUREMENT

CROSS-REFERENCE TO RELATED APPLICATIONS

This application claims benefit of and priority from the U.S. Provisional Patent Application No. 62/236,275 filed on Oct. 2, 2015 and titled "Array of Encoders for Alignment Measurement". The disclosure of the above-identified priority application is incorporated herein by reference.

TECHNICAL FIELD

The present application relate to systems and methods for measurement of wafer-alignment and, more particularly, to improvement of the quality of alignment of the pre-patterned wafer for the following cycle of exposure in an exposure tool.

BACKGROUND

Exposure apparatus (also referred to as lithographic exposure tools) are commonly used to transfer images from a reticle onto a substrate (interchangeably—wafer) during semiconductor processing. A typical exposure apparatus, used for transfer of a pattern from a reticle onto a substrate of interest (interchangeably—a target substrate or a wafer, such as a semiconductor wafer during the semiconductor processing), includes an illumination source, a reticle stage assembly (that positions a reticle within the apparatus), an optical assembly containing projecting optics, and a wafer stage assembly (that positions the target substrate or a wafer). A typical exposure apparatus also includes a measurement system (that monitors positions of the reticle and the target substrate), and a control system that governs operations of various assemblies to adjust, when required, mutual positioning of the reticle and the target substrate. The geometrical features of patterns transferred from the reticle onto the target substrate are very small, which imposes extremely tight requirements on precise positioning of the target substrate and the reticle to manufacture high quality patterned semiconductor wafers.

Driven in part by advances in design of exposure apparatus, the accuracy of the measurement system employed by the exposure apparatus has to be constantly improved. At the same time, there remains a practical limitation of maintaining a relatively small size of the exposure tool, simplicity of its construction, a need for reduced number of moving parts, and high measurement sensitivity.

SUMMARY

Embodiments provide a mark-detecting apparatus configured to detect a mark formed on a mark region of an object. Such apparatus includes a first optical system configured to supply a measurement beam of light towards the object. The apparatus further includes an objective optical system positioned to receive the measurement beam from the first optical system, to form a condensed measurement beam by condensing the measurement beam, and to eject the condensed measurement beam towards the mark region. The apparatus is further equipped with a second optical system disposed to receive a positive-order diffraction beam of light and a negative-order diffraction beam of light through the objective optical system (where the positive-order and negative-order diffraction beams have both been generated at the mark region as a result of diffraction of the condensed measurement beam at the mark region), while the second optical system is configured to interfere said positive-order and negative order diffraction beams of light to form an interference beam of light. The second optical system is configured to co-directionally transmit the positive-order and negative-order diffraction beams regardless of whether there occurs a change of an angle of diffraction of the condensed measurement beam at the mark-region. The apparatus additionally includes an optical detector located to receive and detect the interference beam of light.

Embodiments additionally provide a method for exposing an object to light. The method contains the step of measuring a position of a mark formed at a marked region of an object and exposing the object. The process of such measuring is effectuated by condensing a measurement beam of light produced by a first optical system and directing a condensed measurement beam towards the mark region; transmitting a positive-order diffraction beam of light and a negative-order diffraction beam of light through a second optical system co-directionally to overlap these positive-order and negative order diffraction beams and to form an interference beam; and generating a stage-position measurement signal based on a detector output signal from an optical detector that has received the interference beam. The detector output signal represents a parameter characterizing the mark, while the co-directional nature of transmitting the identified two beams of light through the second optical system does not depend on a change of an angle of diffraction of the condensed measurement beam at the mark region. The method further includes exposing the object to exposing light from a lithographic exposure system that is operably cooperated with the objective optical system and first and second optical systems, at least in part in response to the stage-positioning measurement signal.

Embodiments additionally provide an optical sensor configured for operation with a lithographic exposure tool. The sensor includes (i) a lens system having front and back sides and an optical axis; (ii) a reflector positioned at a first side of the lens system to receive a first portion of an input beam of light, that has propagated through the lens system twice, through a first peripheral portion of the lens system and to change optical parity of said portion of the input beam upon transmission thereof; and an optical interface unit. The optical interface unit contains at least a light input system, disposed at the first side of the lens system to deliver the input beam of light to the lens system along the optical axis, and a light output system disposed at the first side and laterally shifted from the optical axis to receive, during the operation, the first portion of the input beam through a second peripheral portion of the lens system.

Embodiments further provide a related optical sensor configured for operation with a lithographic exposure tool. Such sensor includes an optical system that contains first and second lens systems disposed coaxially about an optical axis; and an optical interface unit. The optical interface unit includes (i) a light input system disposed between the first and second lens systems to deliver a first collimated beam of light towards the first lens system, and (ii) a light output system disposed between the first and second lens to receive second collimated beam of light from the second lens system, the second collimated beam of light including light contained in the first collimated beam of light. The sensor additionally contains an optical wedge positioned across the optical axis between the first and second lens systems.

Furthermore, embodiments provide a method for defining a trajectory of wafer-stage movement during a process of wafer exposure in a lithography exposure tool, effectuated by determining in-plane distortions of at least one pattern on a pre-patterned wafer on a wafer-stage of the exposure tool by simultaneously measuring position-dependent phases of multiple optical signals, each of said multiple optical signals being formed at a corresponding alignment mark defined at the pre-patterned wafer.

Additionally, embodiments provide a method for defining locations of alignment marks for exposure fields on a pre-patterned wafer in a lithography exposure tool, which method includes: (a) with an array of optical encoders of the exposure tool, acquiring measurement optical data representing phases of first optical signals as a function of change of positions of the alignment marks in the exposure tool (while optical signals having been relayed to the optical encoders from respectively-corresponding spatially-periodic alignment marks defined at a pre-patterned wafer); and (b) with an array of said optical encoders, acquiring reference optical data representing phases of reference optical signals delivered to the optical encoders from a reference structure at the wafer stage of the exposure tool.

BRIEF DESCRIPTION OF THE DRAWINGS

The invention will be more fully understood by referring to the following Detailed Description of Specific Embodiments in conjunction with the Drawings, of which:

FIGS. 3A, 3B, 3C, 3D, 3E provide illustrations of spatially-periodic wafer alignment marks configured for use with an embodiment of FIG. 2;

FIGS. 12B, 13A, 13B, and 13C illustrate another related embodiment of at least a portion of the optical measurement sub-system;

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

One of the most critical practical problems in operation of the exposure tool remains the problem of proper overlay of a chosen pattern, imaged from a reticle onto the semiconductor wafer during a given cycle of lithographic exposure, with portions of a pattern to which the wafer (and, specifically, a layer of photoresist carried by the wafer) has been already exposed during a preceding cycle of exposure. With the ever-increasing requirements to accuracy and precision of alignment between the two exposures, there exist at least two methodologies repeatedly used to ensure the quality of the overlay—the use of a microscope system (providing, in operation, the so-called field-imaging alignment, or FIA) and the use of an autofocus system.

The operation of an autofocus system aims to align the target image surface with the focal plane of the projection optics of the exposure tool, and calculates the actually-occurring deviations after performing the determination of the wafer stage tilt and offset. The operation, advantages, and limitations of various incarnations of an autofocus system and, in particular, the operation of encoder heads used in conjunction with autofocus are disclosed elsewhere (for example, in co-assigned application Ser. Nos. 13/134,461; 14/449,371; 14/736,818) and U.S. Pat. No. 8,829,420, and are not discussed here in any substantial additional detail. Disclosure of each of the above-identified patent documents is incorporated herein by reference.

Figure 1:
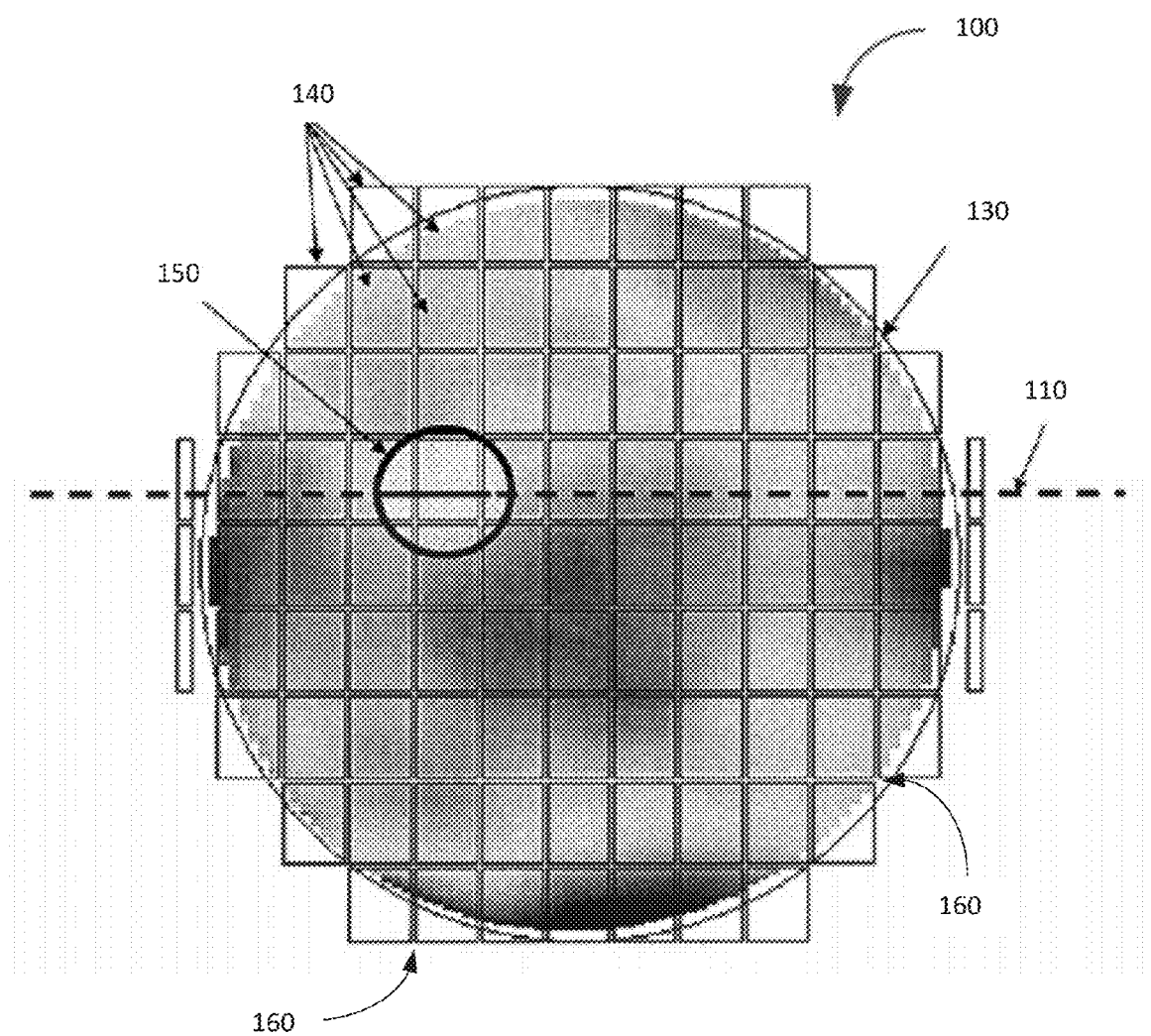
FIG. 1 is a schematic illustration of a grid of exposure fields of a semiconductor wafer.

A typical FIA system, on the other hand, incorporates several microscopes arranged, for example, in line and spaced from one another such that each of the microscopes observes a corresponding alignment mark formed, typically, in the so-called "scribe lines" (that separate one exposure field from another on the wafer; the scribe lines are destroyed when the wafer is diced along these lines into individual semiconductor chips at the end of the manufacturing process.) To this end, as shown schematically in FIG. 1, the wafer 100 having a boundary (perimeter) 130 is shown overlapped with a number of rectangular exposure fields 140 (areas each of which is exposed in one exposure event, and which after the separation from one another along the scribe lines 160 produce wafer chips). The circular line 150 is used to indicate, by encircling, a rectangular foot-print of a particular exposure field from the grid of exposure fields along the single trace path or line 110, which foot-print is an image of a slit with dimensions of about the width of the chip (along the x-axis) and about 5 mm along the y-axis (which is a typical direction of the scan). Each time the wafer is stopped during the scanning process (before the exposure event); the FIA system collects the information about the position of the alignment mark(s) (such as a cross-like pattern) within the field-of-view (FOV) of the microscope objective to assess the quality of alignment of the wafer. Such sequential data collection procedure is rather lengthy, causing a reduction in production output. In addition, understandably, not every exposure field/chip can be covered with just a few microscopes. Simultaneous measurement of alignment of all exposure fields of the wafer with the FIA system remains problematic at least because the number of microscopes equal to a typical number of exposure fields on the wafer (in one case—eighty one) simply cannot fit within the boundary 130 of a typically-dimensioned wafer 100. In addition, the use of multiple microscopes—let alone the number of microscopes comparable with the number of the exposure fields—is prohibitively expensive. Various modifications of the FIA-based procedure, as a result of which the measurement carried out with the use of the microscope(s) remains, understandably do not go to the root of the shortcomings of the FIA-based measurements.

The idea of the present invention stems from a realization that an encoder-head-based measurement of a phase of an interferometric optical signal with the use of a spatially-periodic pattern disposed in a scribe-line of the wafer provides a relative alignment position of a measured area with the modulo $2\pi$ accuracy. Complementing the existing FIA-based measurements (providing the global position of alignment marks) with the relative position derived from the proposed measurement allows for a refinement of such measurement.

Accordingly, as discussed below, a problem of improving the accuracy of a process of overlay of an exposure pattern on an already-patterned wafer without reducing the wafer-exposure throughput is solved by measuring the in-plane distortions of the pattern(s) on the pre-patterned wafer with the use of multiple diffraction gratings located at the already-patterned wafer and an optical system including at least one microscope and an array of optical devices, each of which optical devices is configured to determine a phase associated with a change in position of such diffraction gratings. (The term "in-plane distortion" generally refers to the fact that the grid of chips, or exposures, or patterns exposed on the wafer, deviates from a perfect grid defined in the plane of the wafer. There is some twisting and turning of the grid that must be measured by the system of the embodiment and compensated via the modification of the path along which the wafer-stage is repositioned during the exposure process. The height variations (along the z-axis) are measured by the autofocus system.)

A problem of accurately measuring the alignment of every exposure field on an already-patterned wafer without reducing the wafer-exposure throughput is solved by using diffraction gratings as alignment marks on the patterned wafer and an array of encoder heads each of which is configured to define the positional phase of at least one of such alignment marks. A problem of determining a trajectory of a wafer-stage scanning during the exposure of a wafer in a lithography exposure tool is solved by determining in-plane coordinates of multiple spatially-periodic alignment marks disposed across the wafer by simultaneously measuring position-dependent phases of signals produced by these marks as a result of recombination of light corresponding to different diffraction orders produced by these marks. In various implementations of solutions to the above-stated problems, the measurements are heterodyne measurements performed i) simultaneously at all areas corresponding to all or most of the exposure fields of the wafer, and/or ii) with the use of a homodyne light source, and/or iii) in a fashion not dependent on the wavelength of light used to perform the measurements, and/or iv) with a pre-registration process the results of which allow the accommodation of wafers with differently-dimensioned exposure fields.

In so solving the above-identified problems, different diffraction orders produced by the alignment mark(s) are recombined co-directionally, and such co-directionality does not depend on whether there occurs a change of an angle of diffraction of light incident onto the alignment mark(s).

According to an idea of the invention, an embodiment of the measurement system has an optical measurement sub-system including an optical array of encoders configured to acquire (from spatially-periodic alignment marks defined at a pre-patterned wafer) measurement optical data that represent phases of optical signals as a function of change of positions of such alignment marks in the exposure tool. The pre-patterned wafer is a wafer that has been already exposed to an image of a reticle of the exposure tool during the preceding exposure step, and that is now being aligned for a subsequent exposure to another pattern that has to be overlapped with the previous pattern within the practically-accepted window of spatial accuracy and precision. Some of the alignment marks of the wafer are spatially-periodic structures. The optical array of encoders (referred to as an LIA array) facilitates a low-cost phase-based measurement of a relative in-plane of the wafer alignment of the exposure field(s) with the use of light diffracted from a spatially-periodic alignment structure with the use of a homodyne light source. In addition, at least in one implementation the optical measurement sub-system includes at least one (and, preferably, multiple) FIA optical heads, each conventionally including a microscope and configured to carry out a traditional imaging of additional designated alignment mark(s) within the scribe-lines of the wafer. Such FIA heads may be positionally interleaved with the encoders from the optical array, or, alternatively, can be grouped and/or differently disposed within the optical measurement sub-system. According to the idea of the invention, the optical measurement sub-system is located on the main body of the exposure tool, near the projection lens, so that the alignment of either all shots (exposure fields) are measured simultaneously or the alignments of multiple shots (as a portion of all shots) are measured simultaneously.

Figure 2A:
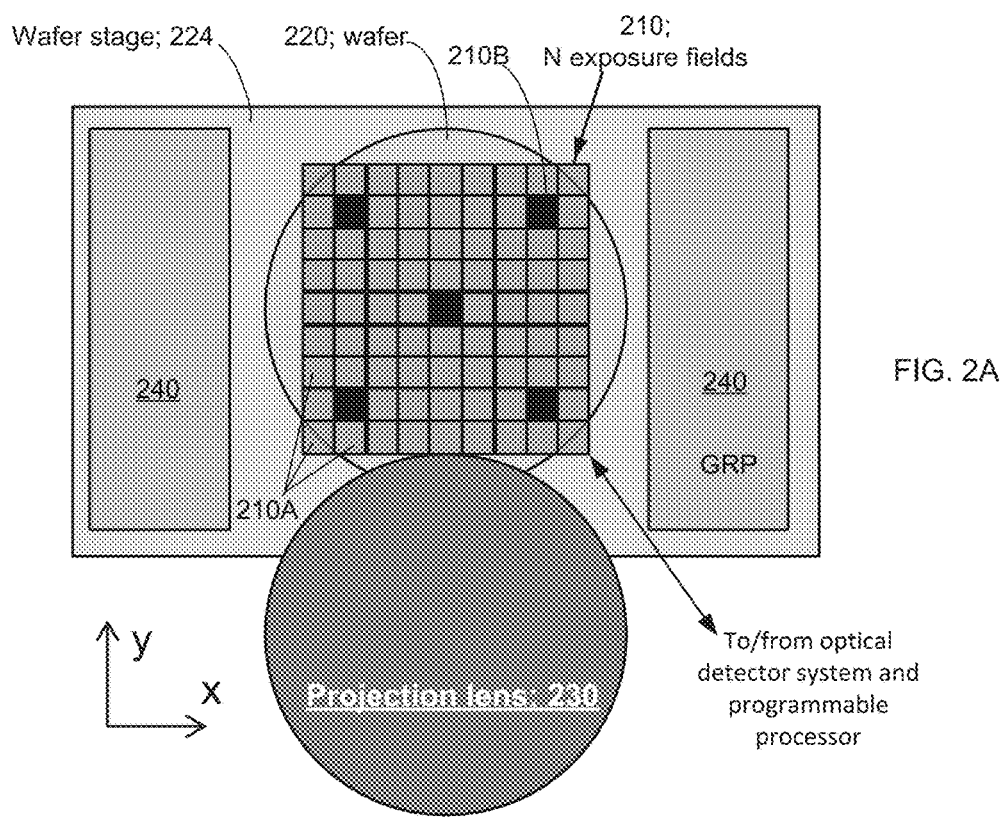
FIGS. 2A, 2B are schematic diagrams showing an embodiment of an optical measurement sub-system of the exposure tool configured to carry out phase measurements at all exposure fields of the wafer simultaneously.
Figure 2B:
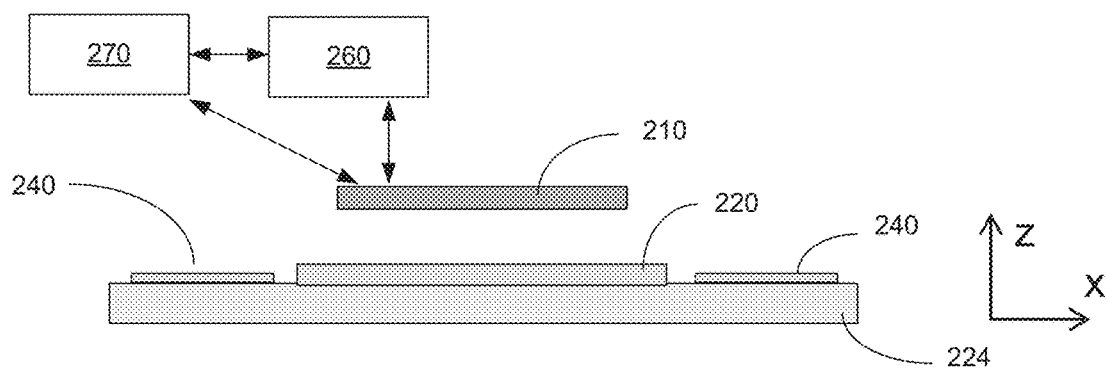

FIG. 2A provides, in top view, an example of the optical measurement sub-system, schematically shown as a rectangular array 210 of optical heads some of which are encoder heads (interchangeably referred to herein as encoders, sensors, LIA, or sensor heads) 210A configured according to an idea of the invention, while the remaining heads 210B are the FIA microscope systems. In this specific example, the LIA encoder heads 210A are spatially interleaved with the five microscope systems 210B to form a symmetric array 210 of optical heads that cover, in total, N exposure fields (in this specific example, N=81) of the pre-wafer 220 and that are removably and repositionably disposed in a plane located above the pre-patterned wafer 220 rested on the wafer stage 224. In operation, the projection lens 230 (the projection optics, PO) of the exposure tool is used to expose the wafer 220 field-by-field, as known in the art. The PO 230 is shown to be shifted away from the wafer 220, while the array 210 of optical heads is shown above the wafer 220. FIG. 2B is a diagram showing the contraption of FIG. 2A inside view. In a specific case, all of optical heads of the rectangular array 210 may be encoder heads 210A, or FIA heads.

Figure 3C:
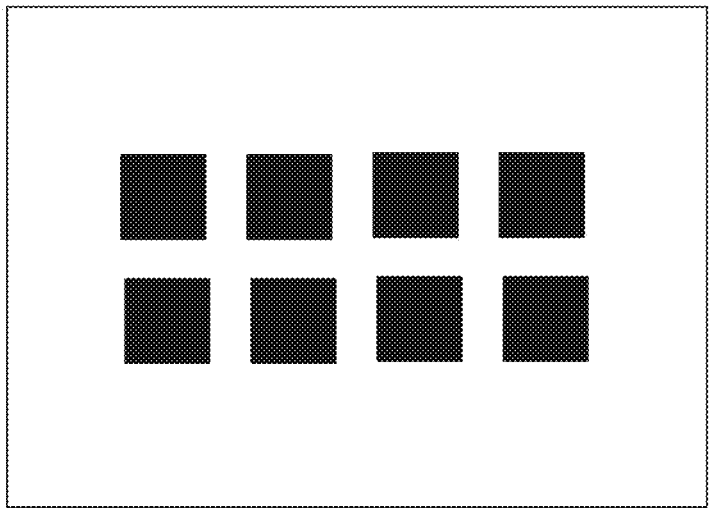
Figure 3C:
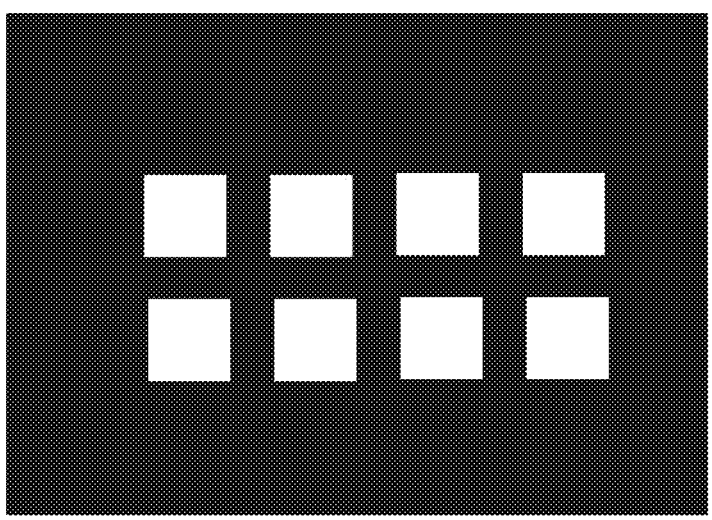
Figure 3D:
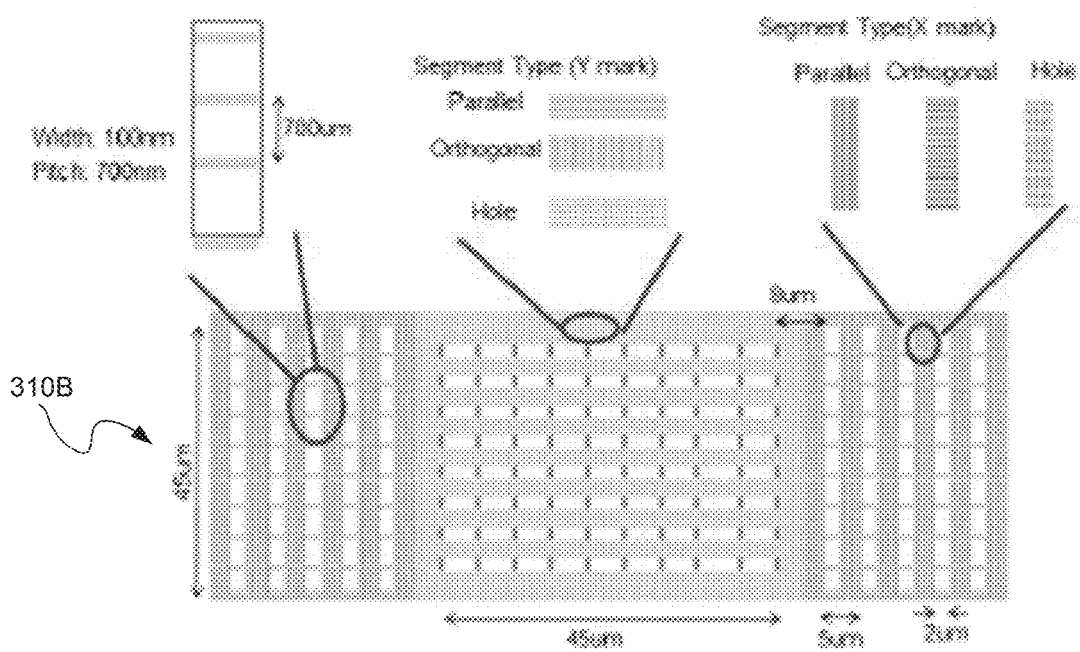
Figure 3E:
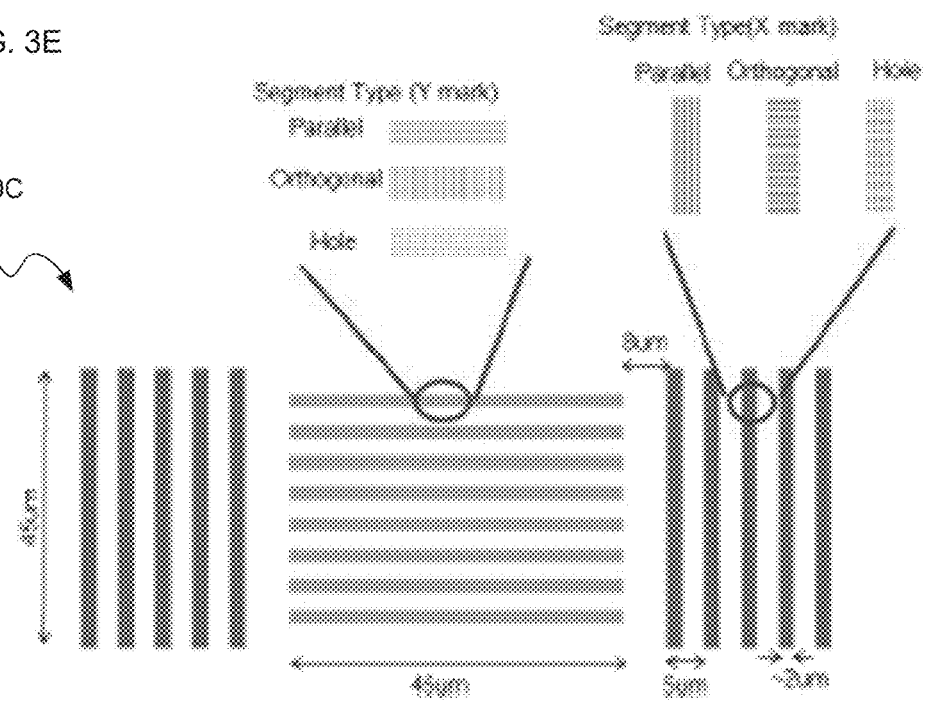

FIGS. 3A, 3B, 3C, 3D and 3E provide illustrations of spatially-periodic structures which, according to an idea of the invention, are carried by the pre-patterned wafer 210 in its scribe-lines. As shown in FIG. 3A, a typical scribe line has a width D of about 50 to 75 microns. A spatially-periodic pattern 310 such as a one-dimensional (1D) and/or two-dimensional (2D) diffractive grating is formed within the scribe-line. Non-limiting examples of the pattern 310 are shown in FIGS. 3B, 3C, 3D, 3E. An implementation of the pattern 310A shown in FIG. 3B includes three sections A, B, and C each of which contains three types of diffraction gratings. (Type 1: 1D grating rulings are directed to form diffraction beams in a plane perpendicular to the wafer stage and containing the y-axis; type 2: 1D grating rulings are direction to form diffraction beams in a plane perpendicular to the wafer stage and containing the x-axis; type 3: a 2D diffraction grating formed by a 2D array of areas having optical properties that differ from the optical properties of the surrounding space, two examples of a type 3 diffraction grating are shown in FIG. 3C). FIGS. 3D and 3E provide related examples 310B and 310C of the in-scribe-line alignment marks that contain spatially-periodic patterns structured according to the idea of the invention. Diffraction grating patterns 310A can be configured as either amplitude or phase or as mixed amplitude/phase gratings, as known in the art.

Referring again to FIGS. 2A and 2B, the array 210 (and, in particular, the array of sensor head 210A of the embodiment) is operably connected (through a data-transfer channel, wired or wireless, and/or an optical channel) to an optical detector system 260 including one or more optical detectors and a data-processing system 270 including tangible, non-transitory data storage and a computer processor. The computer processor is programmed to determine, based on the optical image data collected by such optical detector system from the FIA heads 210B, the absolute position a descriptor (such as an in-plane map of values, for example) of the first-order distortion of the wafer 220. The sub-set 210A of encoder heads effectuates optical phase-based interferometric measurements (configured in a fashion similar to that described in, for example, U.S. Pat. No. 8,829,420, but using an in-scribe-line diffraction structures such as 310A, 310B, 310C instead of the macroscopic gratings affixed to the wafer stage) from which the relative location of a particular exposure shot (with the one-period modulo of the in-scribe-line diffraction grating pattern) is determined.

Further, an embodiment is operationally compatible with (and, in one implementation, is used with) a 2D encoder-based substrate metrology system (not shown) described in, for example, U.S. Pat. No. 8,829,420. The encoder heads (not shown) of such metrology system are disposed above the wafer-stage gratings denoted in FIG. 2 as 240.

It is recognized that encoders used in related art to-date and configured in a fashion similar to that discussed in, for example, U.S. Pat. No. 8,829,420 are not readily suitable for use as encoders 210A in an embodiment at least because the known encoders are configured to perform a heterodyne measurement of phase by delivering to a wafer-stage a collimated beam of light and registering an interferometric signal formed, at an appropriately positioned detector, as a result of interference of light from diffraction orders created from the collimated beam at the wafer-stage. The known 2D encoder(s) are simply not structured to irradiate a target the dimensions of which are as small as the width of a scribe-line while leaving the exposure fields of the pre-patterned wafer that border and define such scribe-line in the dark, so to speak. The freedom to work with collimated beams (both those generated by a light source of the known encoder and those returned to such encoder, in the form of a diffracted beam, from the target portion of the wafer-stage) permits the use of specific retroreflectors and optical relays the operation of which is not limited by the width of a collimated beam of light that is incident there. The dimensional constraints imposed by the idea of the present invention, on the other hand, beg a structural solution for an encoder head (or sensor head) that is operable to produce an optical signal (in reflection of light only from a spatially-periodic structure disposed within the bounds of a scribe-line, as discussed above) that is representative of a phase and/or phase change of light incident onto the spatially-periodic structure from a light source of the encoder head. Based on the best knowledge of the inventors, related art has not provided any solution to such problem at least because such problem has not yet arisen in connection to lithographic exposure tools.

Figure 4:
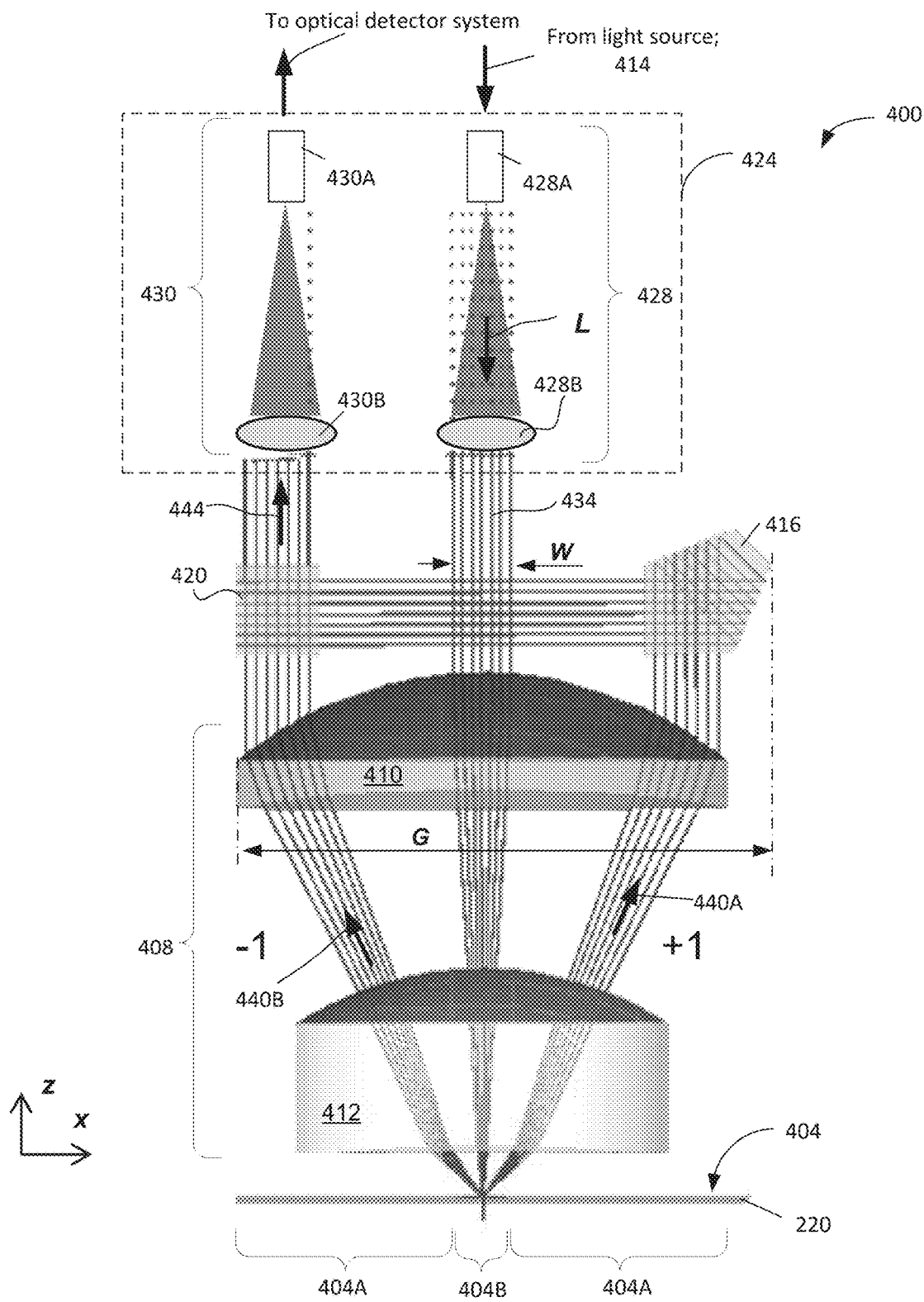
FIG. 4 is a side-view of an embodiment of a sensor head, of the optical measurement sub-system of the exposure tool, configured according to an embodiment.

An example of a sensor-head solution, judiciously configured for use with an in-scribe-line spatially-periodic structures (such as, for example, structures 310A, 310B, and/or 310C), is illustrated in FIG. 4. A schematic diagram 400 of a sensor head 210A, for use with an embodiment of the present invention, is shown juxtaposed against an upper, pre-patterned surface 404 of the wafer 220. Areas of the surface 404 denoted as 404A represent immediately neighboring exposure fields, while the area 404B separating the areas 404A represents a scribe-line on the wafer.

The sensor head (encoder head) 400 includes a compound sensor-head lens 408 (in this specific example—incorporating an optical train or combination of lenses 410 and 412, disposed co-axially about the optical axis 414 of the sensor head, which optical axis is parallel to the z-axis), a reflector 416 (which is shown in a specific embodiment as a pentaprism), and a beam-splitter 420. In reference to a chosen xyz-system of coordinates, in a related embodiment (not shown), the reflector may be configured as a planar mirror disposed in a plane that is parallel to a reference plane containing both the y-axis and the line described as $z=x+1$. The optical components 408, 416, and 420 are complemented by an optical interface unit 424 that includes an input system 428 and an output system 430. The former includes a combination of a light-delivery element 628A (which, in one implementation, may be a single-mode fiber, SMF, optically coupled to a light source, not shown) and an input lens 428B. The latter includes, in a simplest case, a combination of a light-delivery element 430A (which, in one implementation, may be an SMF the distal end of which is optically coupled to an optical detector, not shown) and an output lens 430B. Material of each of the optical components of the head 400 is judiciously chosen to have minimized loss at a wavelength of light L delivered from the optical source through the light-delivery element 428A (and can include, for example, any of glass, plastic materials, thin-film coatings, and/or ceramic materials). The sensor-head lens 408 (objective 408) may be a dioptric system such as this embodiment, a catoptric system (an all-reflection system), a catadioptric system (a reflection-refraction system), or a diffraction optical system. Projection characteristic of the objective 408 may be f-θ, f-sin θ, f-tan θ, to name just a few. Instead of an optical lens, another optical component such as a refractive member (e.g. optical prism), a reflective member (e.g. a mirror), and/or a diffractive member (e.g. a diffraction grating) may be used.

The geometrical parameters and the mutual orientation of the light-delivery element 428A and the input lens 428B are such that the beam of input light L is collimated into a beam 434 with a width W upon transmission through a lens 428B. The value of W is generally between about 1 and about 4 mm (and in one specific implementation, about W=3 mm). The geometrical parameters and mutual orientations of the elements 408, 416, 420 are judiciously chosen to ensure that a dimension of a footprint of the overall contraption 400 onto the wafer does not exceed G=25 mm so that the spatial extent of the projection of each LIA or encoder unit of contraption 400 onto the wafer is smaller than the pitch of the exposure field.

In operation, the beam 434 is converged, spatially condensed in transmission through the lens 408 such as to form a spot of light at the spatially-periodic structure disposed, according to an idea of the invention, in the area 404B of the wafer. Opto-geometrical parameters of the lens 408 are judiciously chosen such that the diameter D of such spot of light does not exceed the width of the scribe-line on the wafer. Diffracting at the spatially-periodic structure of the scribe-line, beam 434 forms in reflection multiple diffracted beams. It is appreciated that in a specific case when the spatially-periodic structure is a 1D diffraction grating, the multiple diffracted beams include only two first-order diffracted beams. In a related specific case when the spatially-periodic structure is a 2D diffraction grating, the multiple diffracted beams include two pairs of two first-order diffracted beams.

As shown in the view of FIG. 4, the two first order diffracted beams 440A, 440B respectively correspond to the +1 and −1 orders of diffraction (that is, positive first-order and negative first-order diffraction beams of light), each of which then propagates in a reverse direction through the lens 408. One of the diffracted beams (shown as 440B) is directed through a beamsplitter/beam-combiner 420 towards the output system 430. Another diffracted beam (shown as 440A) is redirected by the reflector 416 to be recombined, spatially overlapped at least in part with the beam 440B at the beamsplitter 420. When recombined at the beamsplitter, the beams 440A, 440B form an output beam 444 that represents a result of optical interference of the beams 440A, 440B and is delivered to the optical detector system 260 of the sensor head through the output system 430. The reflector 416 and the optical beam combiner 420 are preferably equidistantly separated (or distanced or shifted), with respect to the optical axis of the lens 408 such as to respectively receive the first and second portions of the input beam 434 (which first and second portions, in operation of the embodiment 400, are formed at equal distances away from the optical axis).

The embodiment 400 is configured, therefore, for operation in the lithographic exposure tool to form the first and second portions as first and second beams of light defined by light from the input beam of light that has diffracted at a spatially-periodic alignment mark (of a pre-patterned wafer in optical communication with the exposure tool), when the alignment mark is located between first and second patterns on the pre-patterned wafer.

It is appreciated that the specific implementation of the optical system 400 of the sensor-head is configured to produce a single-pass diffraction of the input light beam L off the wafer, which causes a 2× increase of sensitivity of the sensor head as far as motion along the x-axis is concerned when the two beams are combined. The phase will change by one period when the scribe-line pattern moves along the x-axis by T/2, which is one-half of the pattern period T.

A skilled artisan will readily appreciate that the optical system of the sensor head can be appropriately modified to collect light delivered to the wafer through the optical system after a double-pass diffraction of the input light L off the wafer, in which case the sensitivity of the resulting sensor-head (not shown) to the change of phase of an optical signal received from an alignment mark will be increased to 4×. At the same time, the simpler, 2×-sensitivity embodiment 400 may be operationally preferred to a more complex 4×-sensitivity embodiment in some situations, because— unlike in the case of the use of the 4×-sensitivity embodiment—the use of the embodiment 400 does not require an additional image registration between the two second-pass beams directed to the wafer. In a 4×-sensitivity system such registration is highly preferred, due to the ever-present imperfections of the optics involved.

When the reflector 416 is configured as a pentaprism, as shown in FIG. 4, such reflector changes the parity of the beam 440A upon interaction with the beam. As a result, the remaining even aberrations of the lens 408 are now affecting, modifying the beam 440A in (towards) the same spatial direction, thereby reducing the phase mismatch (including that caused by tilt) between the beams 440A and 440B. Notably, the rotation of the beamsplitter 420 about the y-axis can be employed to change the degree of tilt between the beams 440A, 440B upon recombination at the beamsplitter. If required, auxiliary optical components such as optical filter(s), for example, may be disposed across at least one of the beams arriving at the beamsplitter 420 from the optical system 408.

In a specific embodiment, the combination of the reflector 416 and the beamsplitter 420 represents, therefore, a reflector unit that contains (i) a first light-reflecting member structured to reflect an even number of times (internally to the first light-reflecting member) one diffraction beam of light incident thereon through the objective optical system 408, and (ii) a beam-combining member disposed to receive a beam of light arriving thereto from the first light-reflecting member, to reflect said beam of light, and to transmit another diffraction beam of light arriving thereto through the objective optical system 408. Such a reflector unit is configured, therefore, to reflect at least one of the positive-order and negative-order diffraction beams, incident on the reflector unit, an odd number of times.

Figure 5:
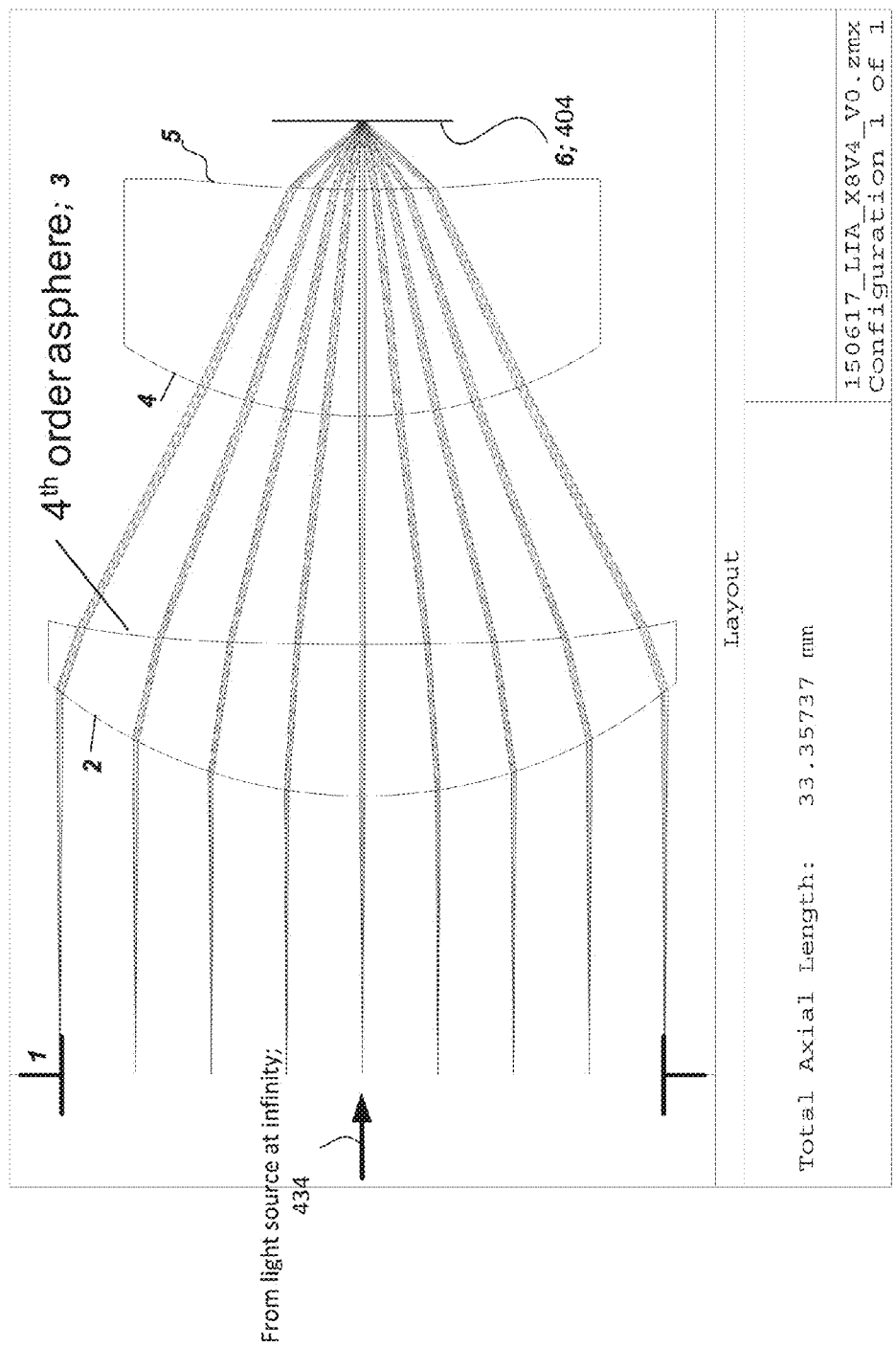
FIG. 5 is a layout of a lens employed by the embodiment of FIG. 4.

While one can envision various designs of the compound lens 408, a specific, not necessarily optimized two-lens example of such compound lens 408 is provided in FIG. 5 and Table 1. Here, surface 0 represents an object at infinity (providing the collimated beam of light 434 as an input beam to the lens 410), surface 1 represents a pupil/diaphragm of the lens 408, and surface 6 represents an image surface (the surface 404 of the wafer). It is understood that, in a related embodiment (not shown) it may be preferred to have the compound lens 408 to be structured as a single-piece-of-glass optical component (such as a triplet or a doublet lens), to prevent a need in relative alignment of the constituent lens elements of the lens 408, simplify the operation of the sensor head, and reduce its cost.

TABLE 1

(in reference to FIG. 5): Description of the compound lens of the embodiment of FIG. 4

| Surface# | Type | Curvature | Thickness | Glass | Semi-Diameter | 4th order Asphere (aspherical surface) |
|---|---|---|---|---|---|---|
| 0 (object) | STANDARD | 0.00E+00 | Infinity | | 0.0000 | |
| 1 | STANDARD | 0.00E+00 | 9.75 | | 10.6061 | |
| 2 | EVENASPH | 5.8100E−02 | 5.31 | S-LAH58 | 11.0000 | |
| 3 | EVENASPH | 6.1677E−03 | 8.00 | | 11.0000 | 3.054089E−05 |
| 4 | EVENASPH | 6.5067E−02 | 7.94 | S-LAH58 | 8.3500 | |
| 5 | EVENASPH | 1.7773E−02 | 2.36 | | 6.3500 | |
| 6 (image) | STANDARD | 0.00E+00 | 0.00 | | 0.1446 | |

Figure 6:
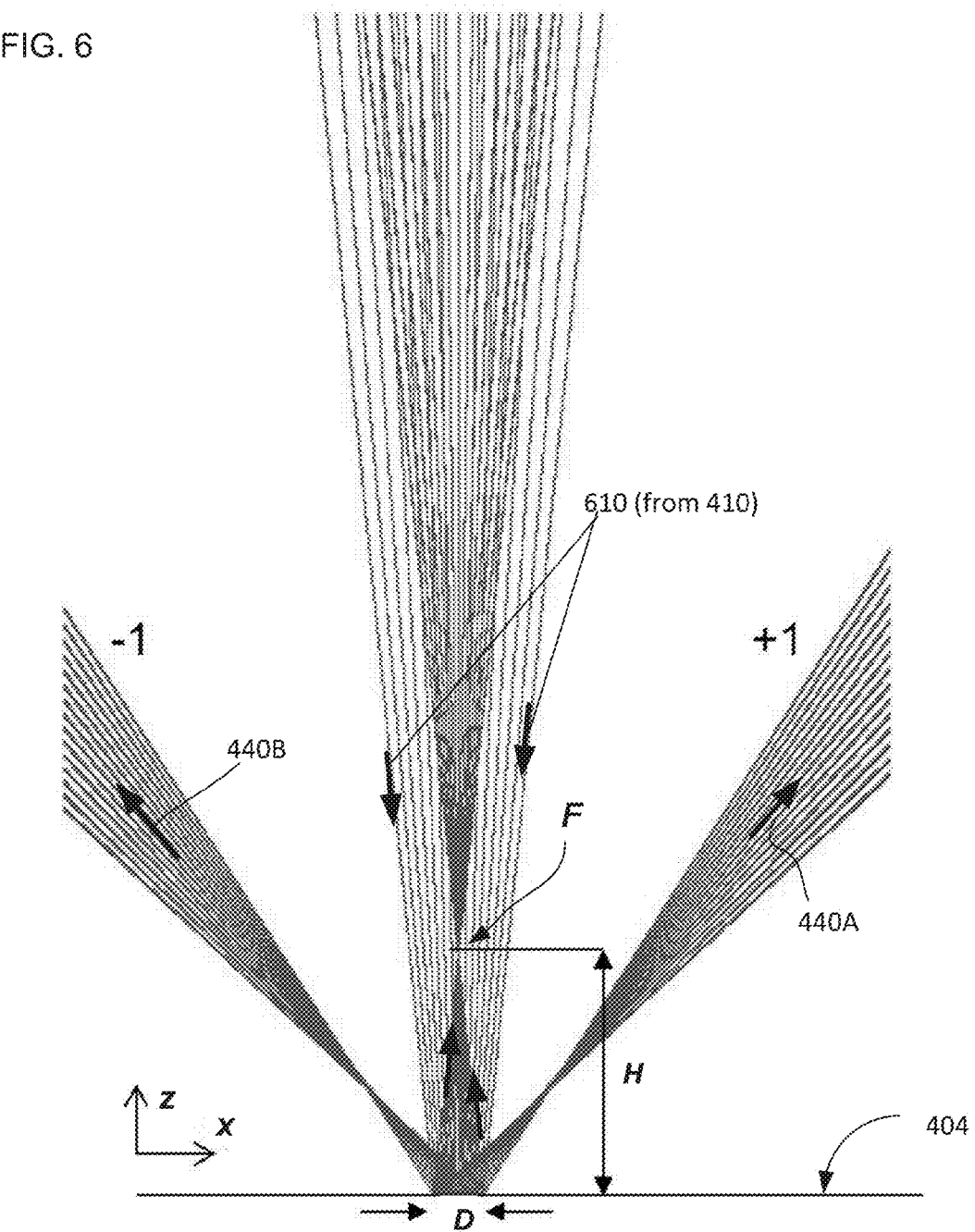
FIG. 6 is a close-up schematic view of an incident light beam delivered by the lens of FIG. 5 towards the pre-patterned semiconductor substrate, carrying a spatially-periodic alignment mark(s) in a scribe-line, and diffracted beams formed by such alignment mark(s)

FIG. 6 provides an expanded view of the light distribution formed by the embodiment 400 near the surface 404 of the wafer. The optics of the embodiment 400 are designed to deliver to the surface 404 of the wafer, upon the transmission of the beam 434 through the lens 408, a beam 610 the focal point F of which is shifted, distanced from the surface 404. Such configuration is intentional, as it allows a substantially complete (and, if required, spatially-variable) coverage of the spatially-periodic structure in the scribe-line with the spot of light D. The numerical aperture of the beam 610, impinging onto the surface 404, is chosen in one example to be about NA=0.11 (for a 3 mm input beam 434), and the lens 408 has a focal length of about f=14 mm. The defocus of about H=230 microns (wafer moved closer to the embodiment 400) with respect to the surface 404 results in an illuminated region of about D=50 micron size on the scribe-line 404B.

The size D of the illuminated region understandably changes, depending on the z-profile of the surface 404. It was empirically determined that, in practice, the Rayleigh range of optics employed by an FIA provides by a rather limited range of practically-acceptable deviation of the wafer from the focus of the FIA, typically on the order of a micron or so. Considering that the depth of focus provided by an LIA from the LIA array is at least an order of magnitude larger (that is, at least 10 microns or several tens of microns or even on the order of 100 microns), the simultaneous operation of the FIA and LIA array in the same optical measurement subsystem is ensured, for any variations of the wafer profile (measured along the z-axis) within the range of defocus of the FIA.

While the defocus H causes a certain amount of aberration in the diffracted beams 440A, 440B, the beams 440A, 440B occupy a very small area of the lens pupil, so the interference between the +1 and −1 diffraction order beams upon recombination of these beams at the component 420 has very high contrast (on the order of about 90% of the maximum expected contrast value, or higher) throughout a reasonable range of the z-profile of the wafer surface.

Notably, the proposed embodiment is operationally resilient to typical misalignment encountered in an exposure tool. When the wafer tilts at an angle θ about the y-axis, a slight change of the angle between the diffracted beams 440A, 440B causes a slight shearing of these beams at the output lens 430B. (In case when the pentaprism is used as a reflector 616, the beams shear in opposite directions. The tilt about another axis—x-axis—does not cause the change of the relative angle between the beams as both beams shear in the same direction.). A 1-mrad tilt between the wafer and the sensor head 400, for example, causes a less than 14 micron shear (Shear=fθ) for both beams, or only about 28 microns of relative shear between these beams. For a W=3 mm diameter beam 434, this results in a less-than-1% contrast loss at the distribution of light 444 at the output lens 430B.

Accordingly, an embodiment 400 is structured to ensure to transmit the positive-order and negative-order diffraction beams, formed during the use of the embodiment for measurements of a characteristic of the pre-patterned wafer 220, in the same direction (or, to codirectionally transmit such diffraction beams) in a fashion that is substantially free or independent from a change of the angle of diffraction of the input beam at mark-region 404B of the pre-patterned wafer 220.

Figure 7:
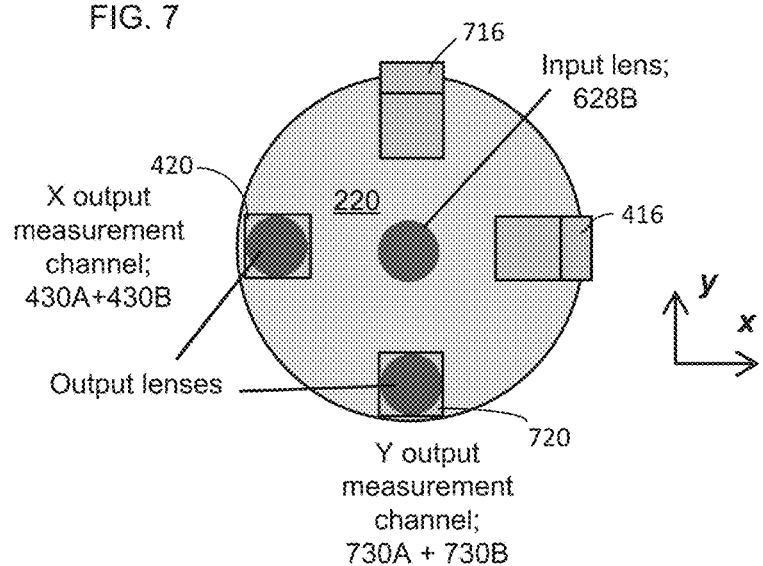
FIG. 7 is a top view schematic diagram of the embodiment of FIG. 4, illustrating a three-dimensional distribution of diffracted beams and operation of the embodiment.

Referring again to FIG. 4, the configuration of the sensor-head is shown in only one side view. This side view provides an illustration of either the operable cooperation of the sensor head with a 1D spatially-periodic in-scribe-line alignment mark or, alternatively, a one-sided view of operable cooperation of the sensor head with a 2D spatially-periodic in-scribe-line alignment mark. Understandably, the structure of the embodiment 400 is extended along the y-axis as well, to facilitate the use of +1 and −1 diffraction beams (formed at the area 404B) in the yz-plane as well. The idea of such structural extension will be readily appreciated by a person of ordinary skill in the art from the diagram of FIG. 7, in which, in top view, a complementary combination of the beamsplitter 720, reflector 716, and the output system 730 (including an optical fiber 730A, not shown, and a lens 730B) are indicated. This complementary combination is configured to collect light formed at the 2D spatially-periodic in-scribe-line alignment mark in the form of +1 and −1 diffraction orders in the yz-plane. It is appreciated that for a 2D spatially-periodic in-scribe-line alignment mark of the embodiment, all four diffracted beams (+1, −1 in the xz-plane and +1, −1 in the yz-plane) originate from the same area in the scribe line, and the encoder head 400 is configured to carry out the phase-measurement and the relative change in positioning of the wafer along the x-axis and along the y-axis at the same time. Notably, no polarization optics are required in an embodiment of the encoder head of the present invention, which produces a significant reduction in cost in comparison with a system employing multiple number of heads, each of which requires quarter-wave plates, polarization beam-splitters and other optics that are notoriously expensive in comparison with regular lenses and prisms, for example.

The principle of the acquisition of optical data with the use of the optical measurement sub-system 210 is based on extraction of phase information from an optical signal formed (at a given wavelength) as a result of interference of +1 and −1 diffracted beams (in a given plane perpendicular to the surface of the wafer 220, such as the beam 444 of FIG.

4, for example). More than one practical methodologies exists in related art to effectuate a measurement of the phase based on data obtained from the interference of two optical beams, as understood by a person of ordinary skill in the art, and since the derivation of the phase data based on the results of such interference is tangential and complementary to the idea of the present invention, such derivation is not discussed herein in any specific detail. In order to effectuate the operation of the embodiment of the optical measurement sub-system 210, the sub-system 210 requires a multiple number (for example, 2 or 4) of optical detectors per an encoder head 210A, 400. Given such configuration, and while practically possible, the use of a Zygo-type heterodyne phase-measurement scheme with the use of a heterodyne light source (as described, for example, in U.S. Pat. No. 8,829,420) may be cost-prohibitive. In case of such contingency, and according to one embodiment of the present invention, a homodyne light source is used. In order to allow for a heterodyne phase-measurement with the use of a homodyne light source, however, an embodiment imparts an additional movement on the wafer 220 (by moving a wafer-stage 224), as discussed below. Such movement is added in between the scanning-steps of the wafer stage, with the purpose to induce opposite phase change for the +1 and −1 diffracted beams which then interfere at a corresponding beamsplitter, as discussed above. The combination of a homodyne light source in an encoder head 210A and such additional movement of the wafer stage facilitate a simple implementation of a heterodyne measurement scheme.

Figure 8A:
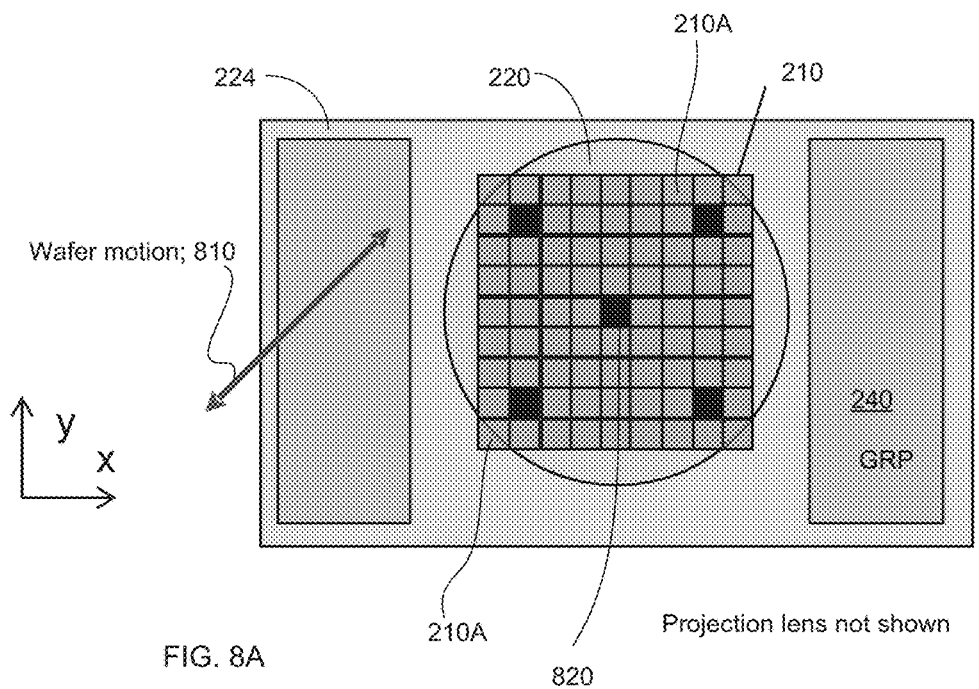
FIGS. 8A, 8B are schematic diagrams showing the additional minute repositioning of the wafer stage configured to provide for required phase-change measurement and, additionally, for registration/calibration of the phase reading with the use of data-processing system of the exposure tool.

Referring again to FIGS. 1 and 2A, if the exposure field patterns on the wafer are aligned to the x- and y-axes of the wafer stage 224, the additional wafer movement can be implemented by moving a stage 224 at a very small distance δd (for example, between 1 and 5 microns for peak-to-valley range or for total distance of wafer travel needed to obtain the required phase change) along a direction defining bisector between the x- and y-axes. This is schematically shown in FIG. 8A, where the additional wafer motion axis is marked with an arrow 810. Based on the controller and encoder head feedback, the phase offset introduced by such motion is readily determined with a processor of the exposure tool. The motion 810 is controlled and defined at such time intervals and speed as to introduce a desired relationship in the measurement channels (of FIG. 7), allowing a heterodyne phase measurement. A particular value of Ed is chosen depending on a period of the spatially-periodic alignment mark (for example, a period of the diffraction grating of the structure 310A) such as to obtain, at the optical detector system 260, at least one full period of a phase-change signal, to ensure a sufficiently high number of sampling phase-data points.

In the situation described in reference to FIG. 4, where the determination of a change in a phase of an optical signal arriving at the optical detector system follow a single pass of each of diffraction beams by the spatially-periodic in-scribe-line alignment mark, such phase is a periodic function with a period proportional to half-a-period of this alignment mark. Considering the overall larger number of optical heads of the array 210 (which includes both the encoder heads or LIA devices 210A and the FIA microscopes 210B), using this many LIA devices 210A presents practical challenges for the registration of the LIA encoders 210 to a chosen point of reference such as a chosen FIA unit (for example, the FIA microscope 820 that is a centrally positioned FIA among the FIA units 210B of the embodiment of FIG. 2A). Such spatial registration can be carried out with the use of the grating plates (that carry the wafer-stage diffraction gratings) 240.

Figure 8B:
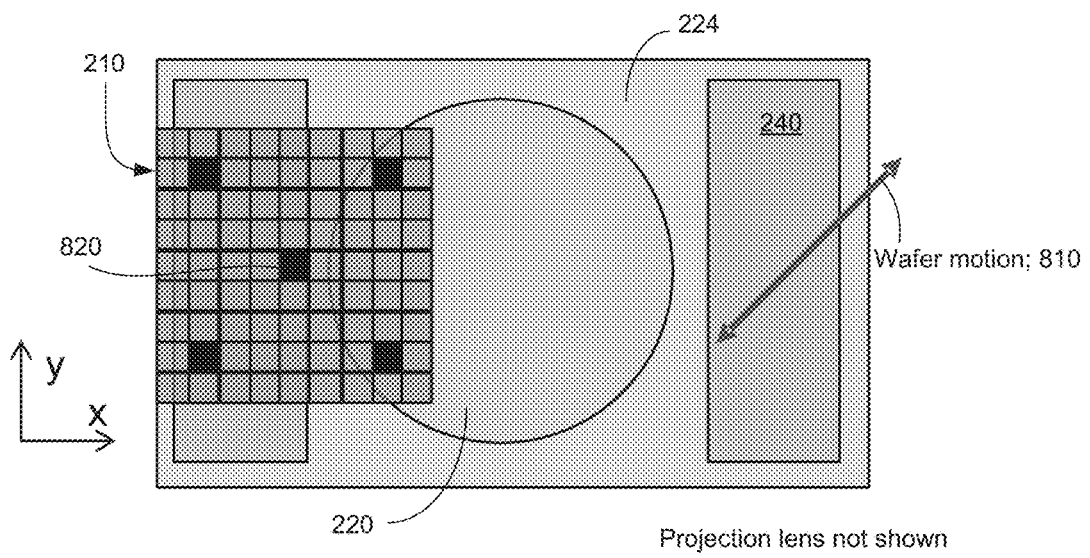
Figure 8C:
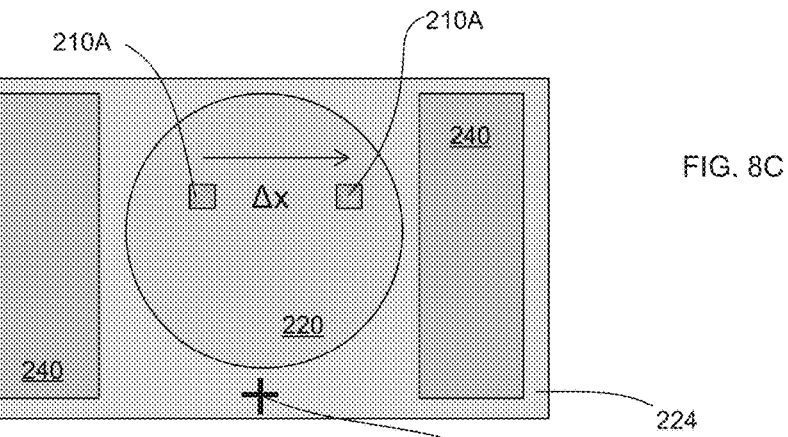
FIGS. 8C, 8D, and 8E are schematic diagrams providing illustrations to an optional calibration procedure configured according to an idea of the invention.
Figure 8D:
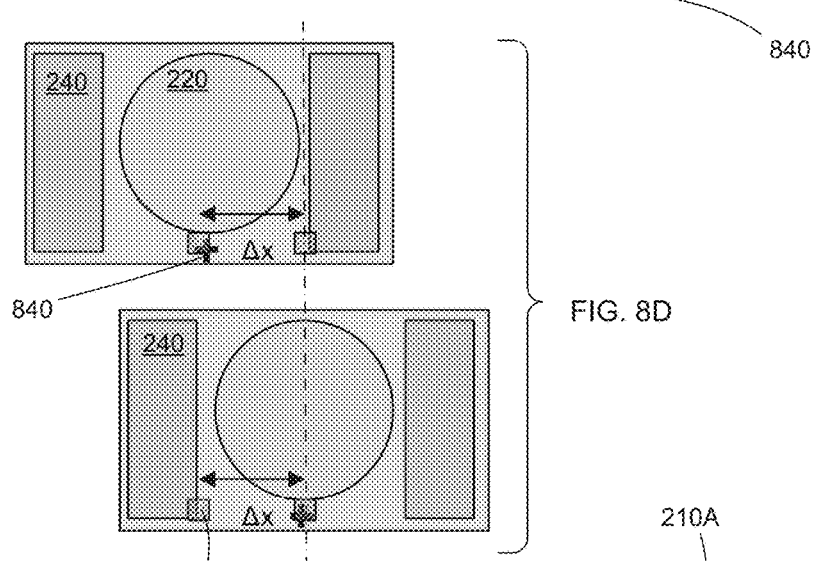
Figure 8E:
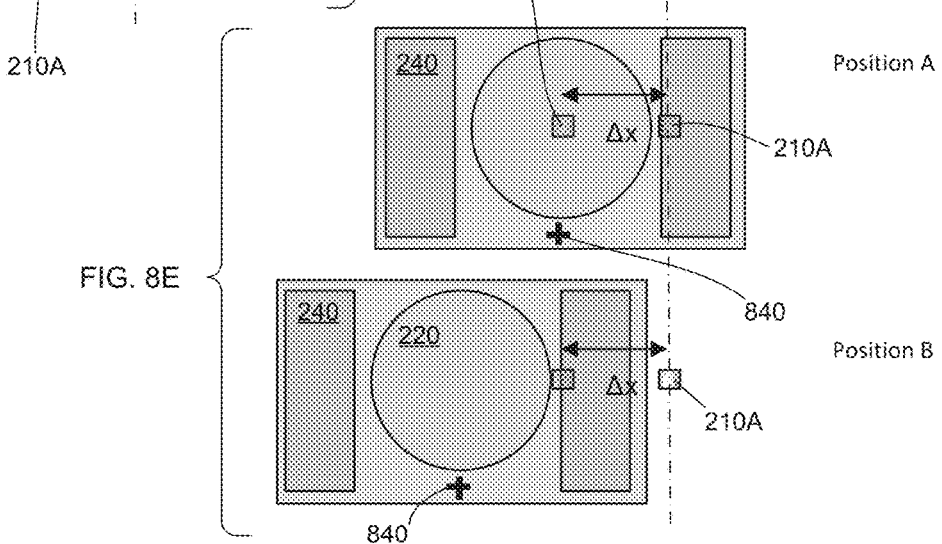

To achieve the required spatial registration, in one implementation the relative positioning of the wafer-stage 224 and the element 240 is laterally changed such as to position the element 240 under the array 210, see FIG. 8B. In this spatial orientation (that is, while the array 210 is positioned above the element 240), the absolute position of a given sensor head 210A can be determined during the same diagonal motion 810. In reference to FIGS. 8C, 8D, and 8E, the following provides an explanation to such determination. For two given LIA devices 210A, of the array 210, that are spatially separated by an unknown distance Δx (considering a case of separation along the x-axis only, for simplicity of illustration) and a given fiducial/alignment mark 840 on the wafer stage, the alignment mark 840 will cause a change of irradiance registered by the LIA sensors 210A, at a Δx-separation that is approximately determined (based on the results of the wafer-stage metrology, FIG. 8C—with the use of encoders when one of the LIA devices 210A of the array sees the feature and then another of the two LIA devices 210A of the array sees the same feature) with some error of, for example, about 0.5 micron. Another way to get the approximate position is to record the signal as the LIA crosses from the wafer stage to looking at the GRPs; the light beams used for the measurement are nearly focused, so the transition from "no signal" to a "non-zero signal" (the latter corresponding to the moment when an LIA device 210A is above the GRP 240), is small and can give the approximate value of Δx, FIG. 8D. In order to get a more accurate and precise value for Δx however, with errors that are smaller than the errors provided by the wafer-stage metrology, the stage 224 is moved, according to the idea of the present invention, such that each of the two LIAs 210A receives a signal from the GRP 240, as shown in FIG. 8E. The phase of the two LTA signals corresponding to wafer-stage positions A and B can be found, sub-period of the phase that is generated from the measurement of the two diffraction orders, and can be used to get their separation on the order of 1 nm. Such calibration process can be done periodically, but not with every wafer (although it could be as the GRPs pass under the LIAs during the normal course of printing a wafer)

During the scan a focused beam across the edge of the GRP 240, the parameters of which are well pre-characterized, the change of the signal acquired by the optical detector would correspond to a shift from the scan across the region with no spatial pattern (i.e., outside of the GRP) to a signal with maximized contrast over a distance of about several tens of microns, for example 50 microns. The phase of the signal provide information about the high accuracy bit, modulo 2*pi. The increase in contrast contains information about the order the system is currently on, relative to the FIA microscope's examination of the edge of the GRP, as well as relative to the other LIA devices that obtain similar contrast curves as the measurement system moves by the GRP edge.

Such calibration process could be conducted periodically during the baseline-check, with the purpose of using the same diagonal motion 810 for alignment measurements of different wafers that undergo a different exposure process (for example, the process of exposure of differently dimensioned exposure fields of shots and/or pattern fields separated by differently dimensioned scribe lines), so the sensor heads 210A could be positioned accurately without the requirement for some other position-measuring system.

While under certain circumstances an embodiment of the optical measurement sub-system can operate while containing only one FIA microscope 210B (and the remaining 210A head to cover the total number of N exposure fields), it is appreciated that multiple FIA units 210B are preferred for proper optimization of the operation of the embodiment.

It is understood, therefore, that embodiments include a mark-measuring system that is structured to measure a position of a mark formed at a mark region of an object the object, in a specific case, may be pre-patterned). Such mark-measuring system includes an optical apparatus, a stage for supporting the object during the operation of the apparatus, a stage-position measurement system, and a data-processing system that contains electronic circuitry including, for example, a programmable processor equipped with computer-readable tangible storage memory). The optical apparatus includes (i) a first optical system configured to supply a measurement beam of light towards the object; (ii) an objective optical system, positioned to receive the measurement beam from the first optical system, to form a condensed measurement beam by condensing said measurement beam, and to direct the condensed measurement beam towards the mark region; (iii) a second optical system disposed to receive a positive-order diffraction beam of light and a negative-order diffraction beam of light through the objective optical system, the positive-order and negative-order diffraction beams of light having been generated at the mark region as a result of diffraction of the condensed measurement beam at the mark region, the second optical system configured to interfere the positive-order and negative order diffraction beams of light to form an interference beam of light. The second optical system is generally configured to transmit the positive-order and negative-order diffraction beams co-directionally, such that a co-directional nature of such transmission is maintained substantially regardless of whether an angle between an optical axis of the condensed measurement beam and the mark region is changed as a result of a tilt of one with respect to another. The optical apparatus further includes optical detector located to receive and detect the interference beam of light and produce a detector output signal. A stage-position measurement system is configured to measure a position of the stage and to produce a stage-position measurement signal. Additionally or in the alternative, the data-processing system is configured to calculate the position of the mark based on, at least in part, the optical detector output and the stage-position measurement signal.

A corresponding method for exposing a pre-patterned object with light in a lithographic exposure system that contains an embodiment includes at least the steps of condensing a measurement beam of light, produced by the first optical system, with the use of the objective optical system and further directing a condensed measurement beam towards the mark region; with the use of a second optical system, transmitting a positive-order diffraction beam of light and a negative-order diffraction beam of light (both of which have been generated at the mark region as a result of diffraction of the condensed measurement beam at the mark) co-directionally to overlap these positive-order and negative order diffraction beams and to form an interference beam. In a specific case, the co-directionality of such transmission does not depend on a change of an angle of diffraction of the condensed measurement beam at the mark region. The method may further include a step of generating a stage-position measurement signal based on a detector output signal from the optical detector that has received the interference beam, while such detector output signal represents a parameter characterizing the mark. The method may additionally include a step of moving the stage based on calculation of the position of the mark with computer-readable data-processing electronic circuitry.

Figure 9:
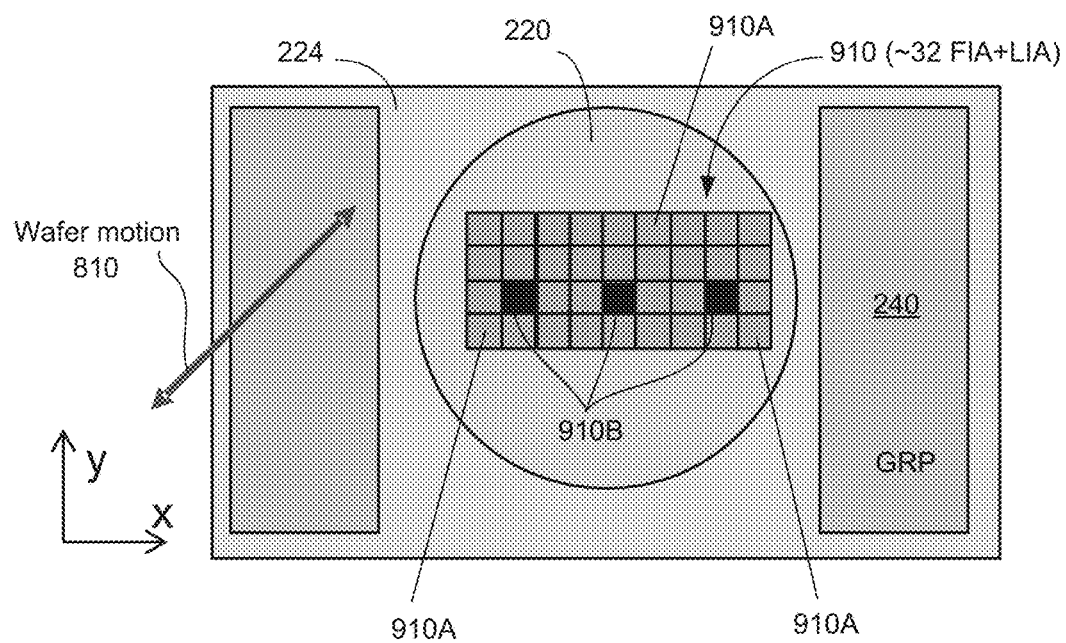
FIG. 9 illustrates a related embodiment of an optical measurement sub-system of the exposure tool configured to simultaneously carry out phase measurements at all exposure fields located in a portion of the wafer within a foot print of the array of optical heads.

A specific situation when the operational space above the wafer on the wafer-stage is limited is addressed in a related embodiment, schematically illustrated in FIG. 9. In such a case, the rectangular array 910 of optical heads is configured to contain a total number of optical heads (including the sensor heads 910A and the FIA microscopes 910B) that is smaller than the overall number of exposure fields 140 on the wafer. The specific embodiment 900 of FIG. 9, for example, is configured to contain thirty-two optical heads (three of 910B and twenty-nine of 810A) in the array 910. The measurement of the alignment of all ninety-six exposure fields 140 of the pre-patterned wafer 220 is carried out, in this case, in three steps, during each of which all exposure field within one-third of the wafer that is covered by (located under) the array 910 are measured simultaneously.

Figure 10:
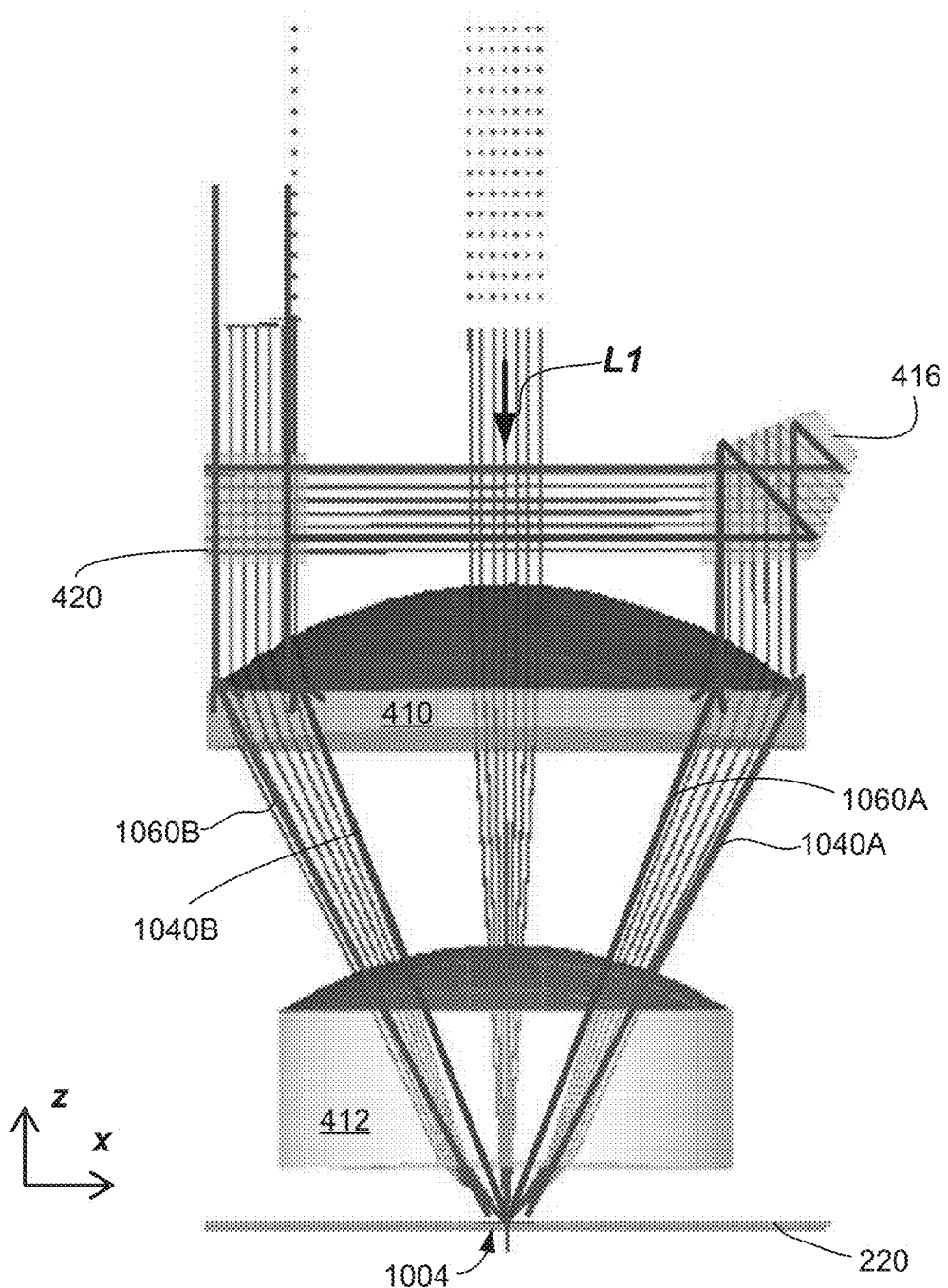
FIG. 10 provides an illustration of a polychromatic operation of an embodiment that employs a pentaprism as a reflector.

Referring again to FIG. 4, it is also worth noting that, while using a pentaprism as a reflector 416 facilitates the use of the embodiment 400 at multiple wavelengths, a related embodiment, in which the reflector 416 of the sensor head 400 does not include a pentaprism (but is, for example, a simple planar mirror) is capable of operating only at a single wavelength (i.e., with a monochromatic light source configured to generate light L). The operation of the embodiment 400 in a polychromatic situation is schematically illustrated in FIG. 10, in which beam L1 that contains light at at least two different wavelengths ($\lambda_1$, $\lambda_2$) is delivered to an in-scribe-line diffraction grating structure 1004 at the pre-patterned wafer 220. The grating 1004 forms two diffracted beams (respectively corresponding to the +1 and −1 orders of diffraction) at each of the present wavelengths. These beams are shown on 1040A, 1040B (+1 and −1 orders at $\lambda_1$) and 1060A, 1060B (+1 and −1 orders at $\lambda_2$), respectively. Pairs of beams diffracted at each of the present wavelengths are propagating through the embodiment 1000 in the same fashion as that described in reference to FIG. 4. As a skilled artisan will readily appreciate, despite the fact that the angle of the light diffracted by the grating positioned in the wafer scribe-line is wavelength dependent (which results in different positions in the back focal plane of the lens for light at different wavelengths), the lens is nominally color corrected such that all wavelengths focus to the same point (below the wafer, as in FIG. 6), and the pentaprism 416 can be judiciously oriented to line up partial beams at different wavelength such that, upon the overlap at the beamsplitter 420, such beams produce respectively-corresponding combined beams 1444 and 1448, each of which forms a wafer-alignment-dependent phase interference pattern at the optical detector unit. The wavelength-dependent optical path difference (OPD($\delta$)) between the +1 and −1 beams at each wavelength needs to be less than half-a-corresponding wavelength. For example, for $\lambda_1$=0.6328 microns; $\lambda_2$=0.6 microns), $OPD_{+1,-1}$(0.6328 microns)−$OPD_{+1,-1}$(0.60 microns) should be smaller than $\lambda/2$, where $\lambda$ is an averaged value of wavelength. Accordingly (and advantageously in comparison with the embodiment where the reflector 410 is a single mirror), an embodiment of the sensor head 210A utilizing a Penta prism as a reflector 416 and a color-corrected lens combination 410, 412 can be configured to perform measurements with a broad-band light L1 (the spectrum of which extends from, for example, 500 nm to 900 nm, or across another spectral several-hundred nanometer range in the visible portion of the spectrum). It is as a result of the ability to perform the measurements with a broadband light that the optical measurement subsystem of the exposure tool gains the capability to perform heterodyne alignment measurements of pre-patterned wafers carrying resist layer with various thicknesses. (Indeed, thin resist layers on a wafer can cause very low reflectivity for light at certain wavelengths, for a given process, by forming destructive interference of corresponding light. Having a tunable light source and optics that can work at a broad(er) range of wavelengths may facilitate the finding of a suitable wavelength range within which such destructive interference is minimized (or even not present), and to use such wavelength range to conduct reliable measurements. (In case the desired broad(er) spectral range of the source is such that the corresponding limited temporal coherence of the light source causes a problem by limiting the operation of the embodiment within such broad(er) spectral range, one appropriate solution may be to split the input beam into two input beams prior to 428A in FIG. 4. An optical delay is then introduced for one of the two beams, which delay is equal to the extra phase delay (or OPD) experienced by the 440A side beams in FIG. 4. In this case, there will be four and not two beams at each of the diffraction orders. The first, non-delayed input beam creates a −1 and +1 beam, and only the +1 beam is used. The second input beam, the delayed beam, creates a −1 and +1 beam, and this −1 beam is interfered with the +1 from the non-delayed beam, to end up with the same total delay and will be temporally coherent enough to interfere.)

It may be additionally preferred that the light source used in such embodiment of the sensor head have high spatial coherence to remain spatially coherent throughout the optical path within the pentaprism to still produce interference fringes upon the exit of light from the beamsplitter 420 towards the optical detector system 260.

Examples of Related Embodiments

Figure 11A:
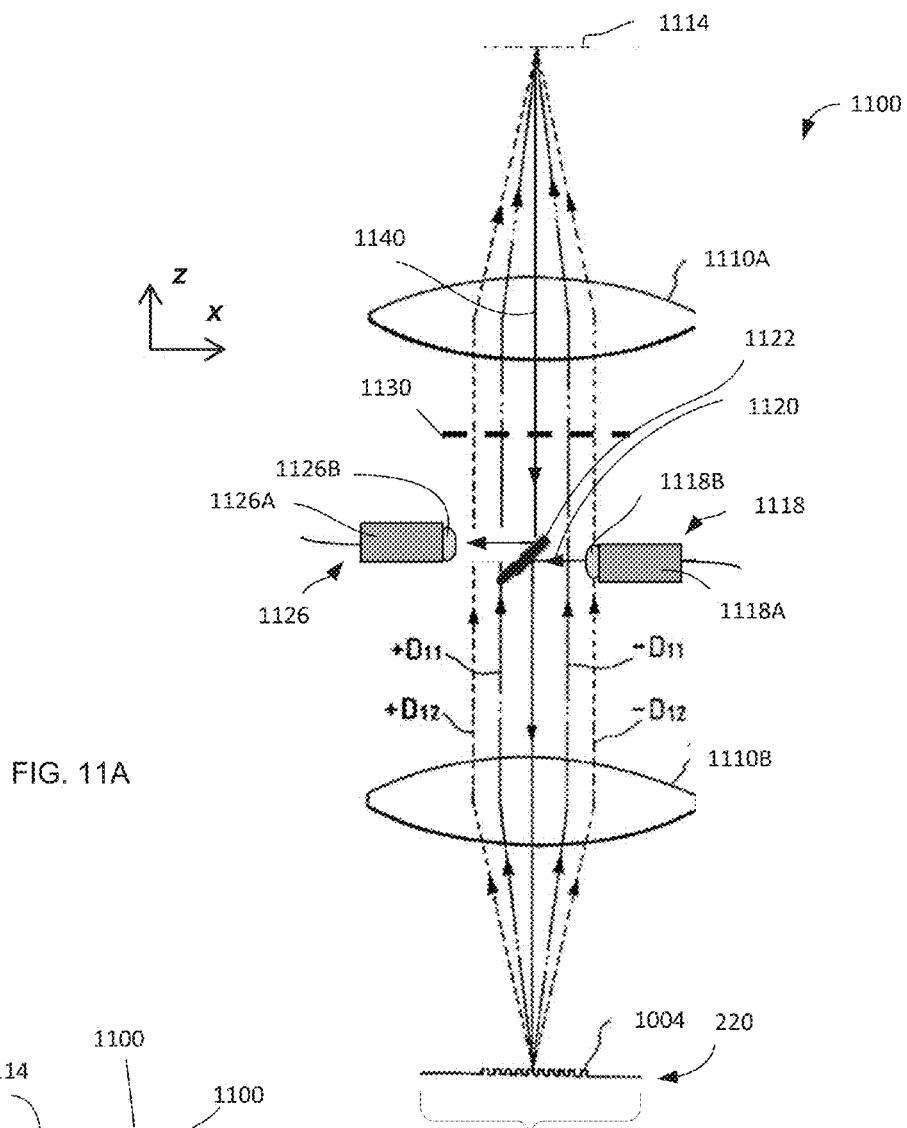
FIGS. 11A, 11B, 11C, and 12A illustrate a related embodiment of at least a portion of the optical measurement sub-system.
Figure 11B:
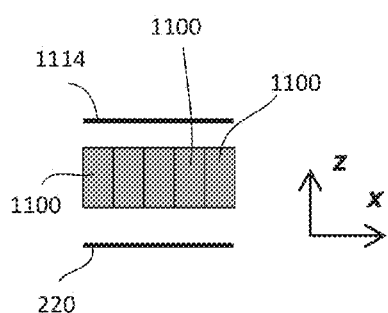
Figure 11C:
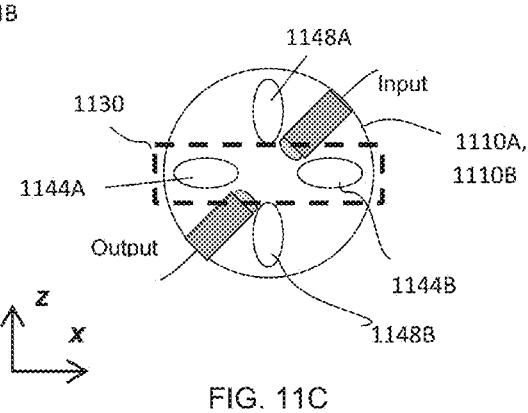

In reference to U.S. Pat. No. 6,034,378, the entire disclosure of which is incorporated by reference herein, FIGS. 11A, 11B, 11C present a related embodiment 1100 of the optical measurement sub-system, which includes a pair of compound lenses (or lens systems, comprising multiple lenses) 1110A, 1110B that are coaxially positioned between a reference diffraction grating 1114 of the system and the wafer in-scribe-line diffraction grating structure 1004. The system 1100 also includes (i) an input optic 1118 containing an optical fiber 1118A and a lenslet 1118B disposed to collimate the light output delivered from the facet of the fiber 118A to define a collimated optical beam 1120 in a plane transverse to the common optical axis of the lenses 1110A, 1110B (such as, in one example, the xy-plane as shown); (ii) a fold mirror 1122 (with two reflective surfaces on the opposite sides of the mirror); and (iii) an output optic 1126 containing optical fibers 1126A disposed parallel to the plane that transverse to the common optical axis of the lenses 1110A, 1110B (such as, in a non-limiting case xy-plane), and lenslet(s) 1126B disposed such as to focus collimated beam(s) of light that have been reflected by a reflective surface of the fold mirror 1122 onto facet(s) of the respective fiber(s) 1126A. The system additionally includes an optical wedge 1130 (an optical prism with a shallow angle between its input and output surfaces), schematically shown in dashed line and positioned between the lens 1110A and the fold mirror 1122 across the optical axis of the lenses 1110A, 1110B. Instead of at least one of lenses 1110A, 1110B, an optical component such as a refractive member (e.g. prism), a reflective member (e.g. mirror), and/or a diffractive member (e.g. diffraction grating) may be used. Instead of the diffraction grating 1114, a reflection type spatial light modulator may be used. A direction of a ridgeline of the optical wedge 1130 may be chosen to be a z-direction or an x-direction. Instead of the optical wedge, a diffractive optical element such as a diffraction grating having a pitch that varies in predetermined direction (e.g. z-direction or x direction).

The input collimated beam of light, 1120, delivered from an external source of light into the measurement sub-system 1110 via the input optic 1118, is reflected by the fold mirror 1122 to be redirected along the optical axis (not shown) of the lenses 1110A, 1110B towards the wafer to be focused on the spatially-periodic 2D diffraction structure 1004 in the scribe line 404B on the pre-patterned wafer. In reflection, the grating 1004 forms four diffracted beams (+1 and −1 orders of diffraction in plane xz, and +1 and −1 orders of diffraction in plane yz, schematically shown as $+D_{11}$, $-D_{11}$ and $+D_{12}$, $-D_{12}$) collimated by the lens 1110B and further refocused by the lens 110A onto the reference grating 1114.

The reference grating 1114 is either part of the LIA system, attached to the array of sensors, or it is fixed (for example, to the metrology frame), depending on the specifics of the embodiment. As a result, the LIA array is configured to be movable relative to the grating 1114 to enable adjustment for different processes. As the reference grating 1114 and the measurement (in-scribe line) grating 1004 form an optically conjugate pair of elements as part of the sub-system 1100, it is appreciated that a pitch of the spatial periodic structure of the grating 1114 and the pitch of the spatially-periodic structure of the grating 1004 are related through the value of optical magnification provided by the pair of lenses 1110A, 1110B. In a special case of unit magnification (m=1), for example, the respectively-corresponding pitches of the gratings 1114, 1004 are equal.

The collimated by the lens 1110B diffracted beams $+D_{11}$, $-D_{11}$ and $+D_{12}$, $-D_{12}$, which are spatially separated in the xy-plane, traverse the optical wedge along the optical axis common to the lenses 1110A, 1110B such that a pair of beams diffracted by the grating 1004 in one plane (such as xz-plane, for example), is angularly tilted or inclined with respect to another pair of beams diffracted by the grating 1004 and with respect to the optical axis. The so-angularly-titled with respect to one another pairs of diffracted beams continue to propagate, as collimated beams, through the lens 1110A and are focused onto the reference grating 1114, which combines the +1 and −1 order diffracted beams of one pair of beams into a single beam, and combines the +1 and −1 order diffracted beams of another pair of beams into another single beam while redirecting both of the so-combined beams (schematically shown only with a single arrow 1140) along the optical axis through the equi-thick areas of the wedge 1130 towards the fold mirror 1122 and further, upon reflection by the mirror 1122, towards the output 2-fiber optic 1126. Since the first and second optical beams formed by combining the respectively-corresponding diffraction orders at the grating 1114 are transversely shifted with respect to one another (as seen, for example, in plane xy), the output lenslet(s) 1126B couple one of the combined beams into one optical fiber of the output optic 1126 and another combined beam into another fiber of the optic 1126, thereby separating the two output signals to separate fibers (and thus separate detectors) and providing a basis for determining the sought-after optical data representing phases of reference optical signals delivered to the optical encoders from the measurement in-scribe-line rating 1004 at the wafer.

FIG. 11C shows the simplified view of a part of the system 1100 observed while looking downwards towards the wafer (towards the grating 1004), where the oval 1144A represent optical beams $+D_{11}$, $-D_{11}$ diffracted at the grating 1004 in the xz-plane while ovals 1144B represent optical beams +$D_{12}$, –$D_{12}$ diffracted at the grating 1004 in the yz-plane. Specifically, the oval shape represents $1^{st}$ diffraction order beams spatially dispersed when light is polychromatic, with the outer portion of a given oval (the portion nearing the circular line showing the boundary of lenses 1110A, 1110B) corresponding to the longer wavelengths and the inner portion of the given oval representing shorter wavelengths. The dashed line representing the wedge 1130 is intended to indicate that the optical dimensions of the wedge 1130 that the pairs of beams (+$D_{11}$, –$D_{11}$) and (+$D_{12}$, –$D_{12}$) traverse are not equal to one another.

Figure 12A:
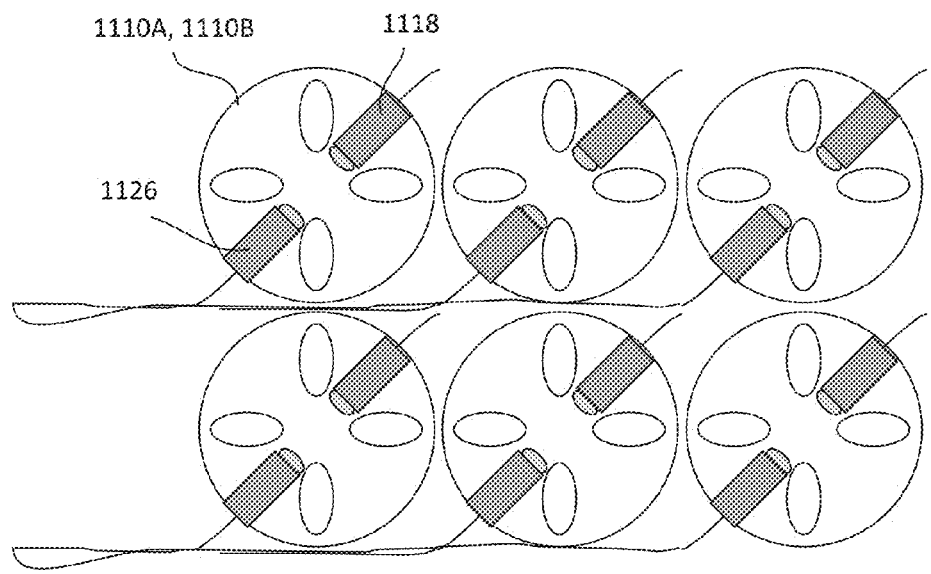

FIG. 11B and FIG. 12A schematically illustrate a related embodiment of the system of the invention equipped with and operating an array of sub-systems 1100 each of which contains a respectively corresponding pair of input and output optics 1118A, 1118B. In FIG. 11B, each of the five shown rectangles represents an independent sub-system 1100 aggregately forming—in the specific shown case—an array of five simultaneously employed sub-systems 1100.

Notably, the reflective grating 1114 can be changed between the independent processes of wafer exposure to match the particular process and/or a separate respectively-corresponding grating 1114 can be used for each of the sub-systems 1100 in the array of FIGS. 11B, 12A. Alternatively, a single grating 1114 can be used to span the entire exposure system that utilizes an array of the sub-systems 1100.

One of operational advantages of the proposed contraption 1100 is that the wedged optical plate 1130 is structured to introduce the off-axis shift (that is, angular shift with respect to the optical axis and with respect to one another) between the directions of propagation of the two beams (the first containing overlapped diffracted beams +$D_{11}$ and –$D_{11}$ and the second containing overlapped diffracted beams +$D_{12}$ and –$D_{12}$, both returned towards the fold mirror 1122 by the grating 1114) for coupling of the corresponding of these two beams in the corresponding of the two output fibers 1126A (spans the +1/−1 orders), as discussed above. Owning to the presence of the optical wedge 1130, the beams diffracted by the gratings 1004 in the xz-plane (beams +$D_{11}$ and –$D_{11}$) once recombined by the grating 1114, as well as the beams diffracted by the gratings 1004 in the yz-plane (beams +$D_{12}$ and –$D_{12}$) once recombined by the grating 1114, are spatially recombined by regardless of their spectral content. Accordingly, provided that the combination of the lenses 1110A and 1126B is color-corrected, the contraption 1100 remains substantially operationally insensitive to the deviation of the operational wavelength of used light from the target wavelength. It also allows the system to change the wavelength of the source prior to the input collimator (1118A) and have it still work as desired, with no other adjustments required. This allows the system to work for different processes, which may have different thicknesses of resists or other layers on top of the scribe lines. In the example shown in FIG. 11, the optical wedge 1130 is arranged in a pupil space (a space containing the pupil) of lenses 1110A, 1110B. Instead of using the optical wedge 1130, a beam shifter such as inclined plane-parallel plate may be used. The beam shifter may be arranged between the lens 1110A and the reference grating 1114, and/or a wafer-side space of the lens 1110B.

Figure 12B:
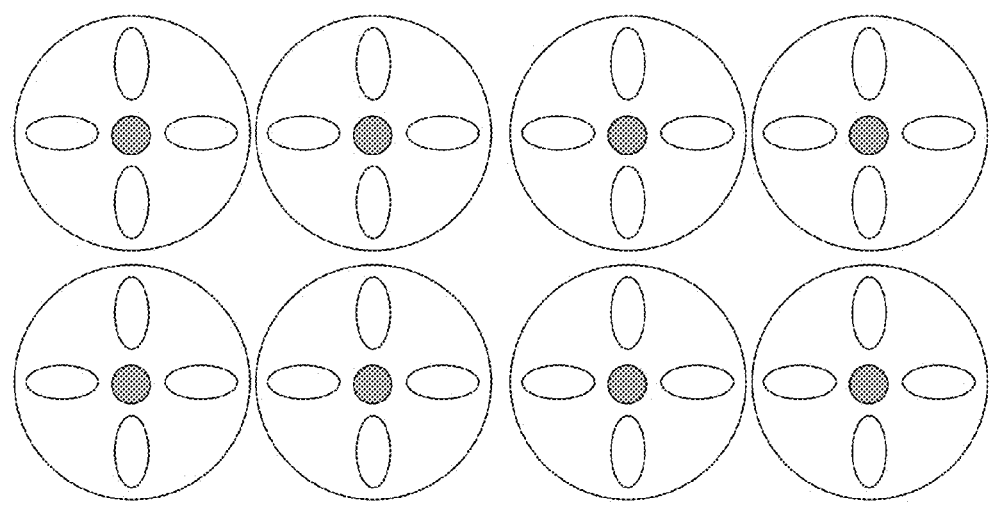
Figure 13B:
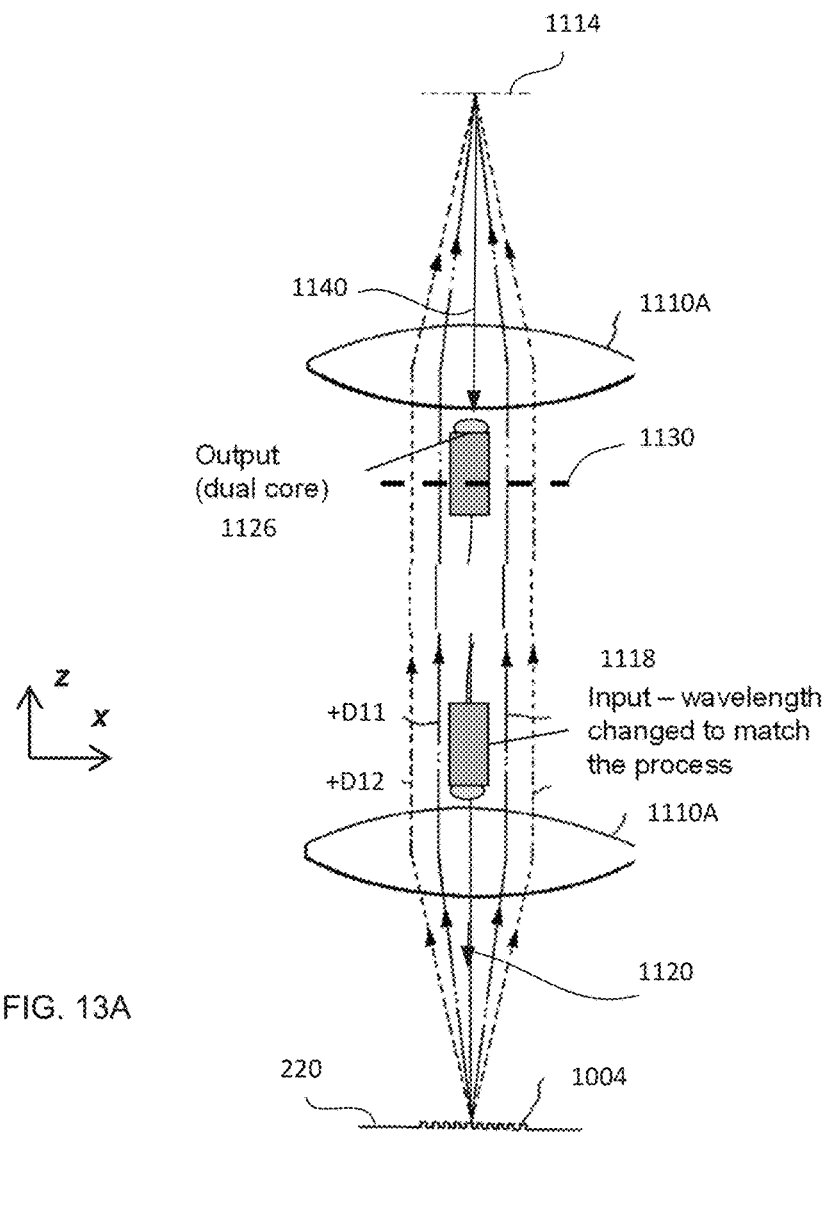
Figure 13B:
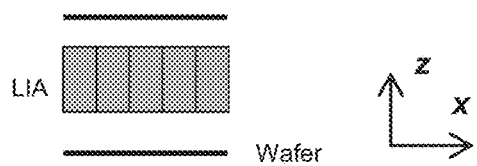
Figure 13C:
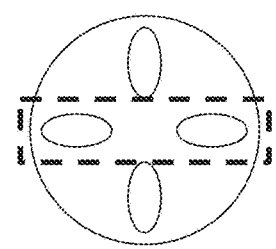

FIGS. 13A, 13B, 13C schematically illustrate an embodiment 1330 related to that of FIGS. 11A, 11B, 11C but simplified in that it does not contain a fold mirror. Here, the input optic 1118 and the output optic 1126 are positioned along the optical axis that is common to the lenses 1110A, 1110B such that the input light collimated by the lens of the optic 1118 is delivered to the in-scribe-line grating structure 1004 on the wafer 220, while the pairs of beams diffracted by the grating 1004 in the xz- and yz-planes, respectively, are recombined by the reference grating 1114 to form two beams of light (shown as 1140), each of which is then coupled by the lenslet of the input optic 1126 into a corresponding one of the two optical fibers of the optic 1126 and delivered, appropriately, to the optical detector. FIG. 12B schematically illustrates a top view of the array containing eight sub-systems 1300 configured for simultaneous use in the exposure system of the embodiment.

Figure 14A:
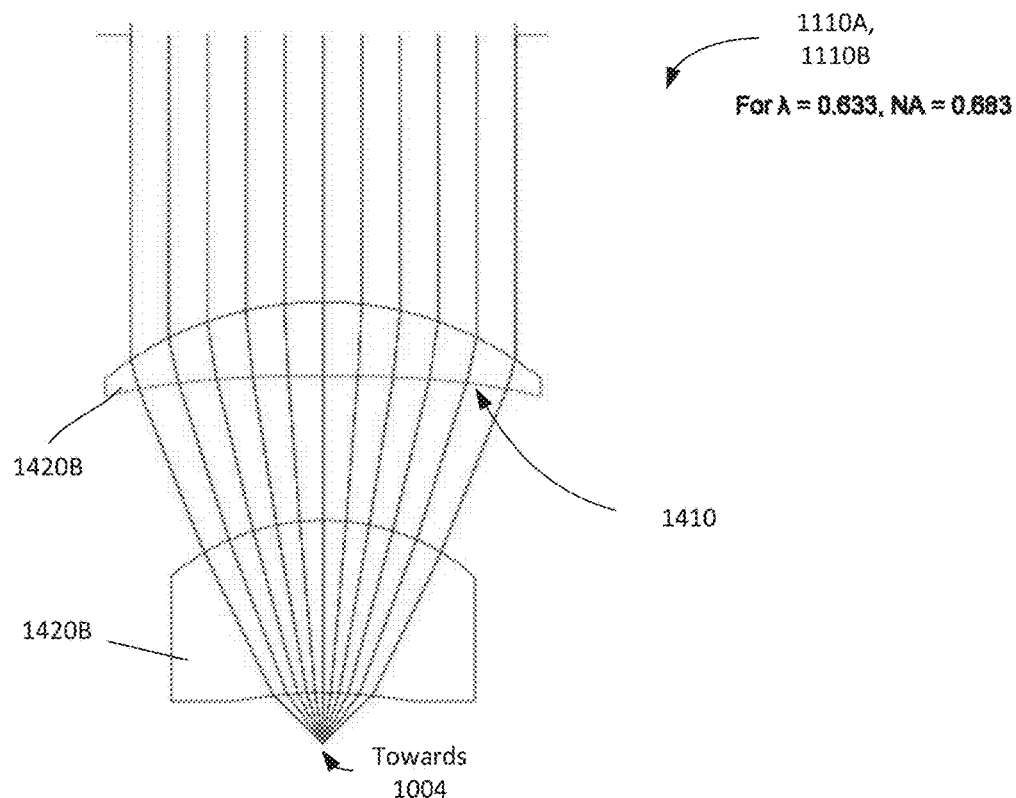
FIGS. 14A, 14B provide schematic illustrations of optical designs of a compound lens for use with embodiments of FIGS. 11A, 13A.
Figure 14B:
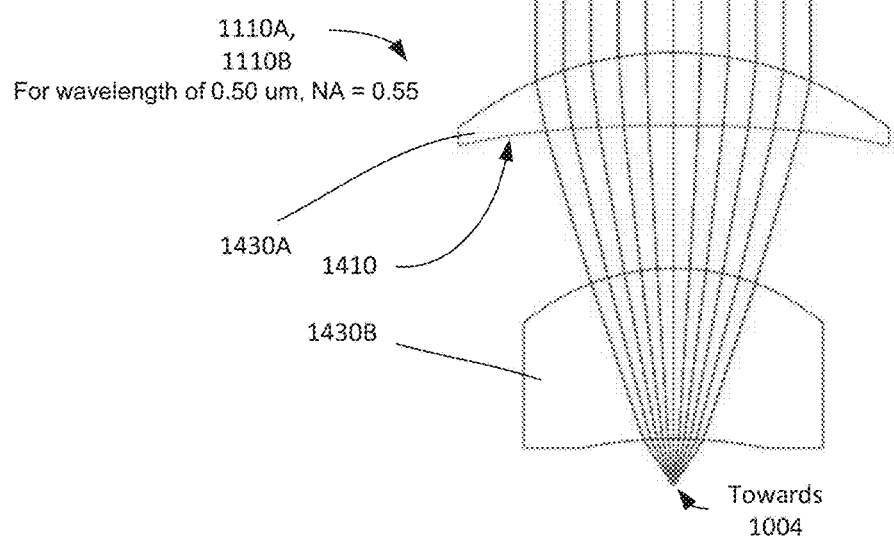

Examples of the design of the lens 1110A, 1110B of used in the embodiments 1100, 1300 is provided in FIGS. 14A, 14B. Here, care is preferably taken to avoid lens surfaces that are concentric with one another and/or concentric with a surface of the wafer to reduce the parasitic optical feedback returned by the wafer surface in reflection of light incident thereon through the lenses 1110A, 1110B. FIGS. 14A, 14B provide examples in which the lens 1110A, 1110B is a two-element lens with one aspherical surface (marked as 1410). The elements of the embodiment of FIG. 14A include lenses 1420A, 1420B, while the embodiment of FIG. 14B includes lenses 1430A, 1403B. ZEMAX data representing the optical train of FIG. 14A is provided in Table 2.

TABLE 2

(in reference to FIG. 14A, monochromatic design): Description of the compound lens such as lens 1110A or 1110B.

| Surface # | Type | Comment | Curvature | Thickness | Material | Semi-Diameter | Conic | 4th order term |
|---|---|---|---|---|---|---|---|---|
| 0 | STANDARD | | 0.00 | Inf. | | 0.000 | 0.00E+00 | 0.00E+00 |
| 1 | STANDARD | Stop | 0.00000 | 9.74986 | | 10.606 | 0.00E+00 | 0.00E+00 |
| 2 | EVENASPH | | 0.05214 | 4.06504 | S-LAH58 | 12.000 | 0.00E+00 | 0.00E+00 |
| 3 | EVENASPH | | 0.01030 | 7.99998 | | 12.000 | 0.00E+00 | 1.901261E−05 |
| 4 | EVENASPH | | 0.07757 | 9.51374 | S-LAH58 | 8.350 | 0.00E+00 | 0.00E+00 |
| 5 | EVENASPH | | 0.03998 | 2.81970 | | 6.350 | 0.00E+00 | 0.00E+00 |
| 6 | STANDARD | Wafer | 0.00000 | 0.00000 | | 0.023 | 0.00E+00 | 0.00E+00 |

Design for the compound lens of FIG. 14B is the same as that in Table 2, except the last distance (between surfaces 5 and 6) changes from 2.82 mm to 2.618 mm. Both designs are monochromatic design, but the wafer/LIA distance can be changed at the discretion of the used to compensate for defocus caused by operation at different wavelengths. In operation, it may be preferred that light at one wavelength be used for a given process, while achromatic design of any of the lenses 1110A, 1110B remains within the scope of the invention.

In one example, and considering the grating pitch of about 1 micron and the operational wavelength of 633 nm, the angle of diffraction at the grating is 39.257 degrees, so the NA of the lens is about $1*\sin(39.257)=0.6328$; to accommodate the NA of the beam incident on the lens of about 0.1, the overall numerical aperture of the lens 1110A, 1110B should be about $0.628+0.05=0.6828$ or thereabout. In general, according to the idea of the invention, the minimum NA of the lens 1110A, 1110B is $NA_{min}=(\lambda/T+0.05)$, T being the grating pitch.

Figure 15:
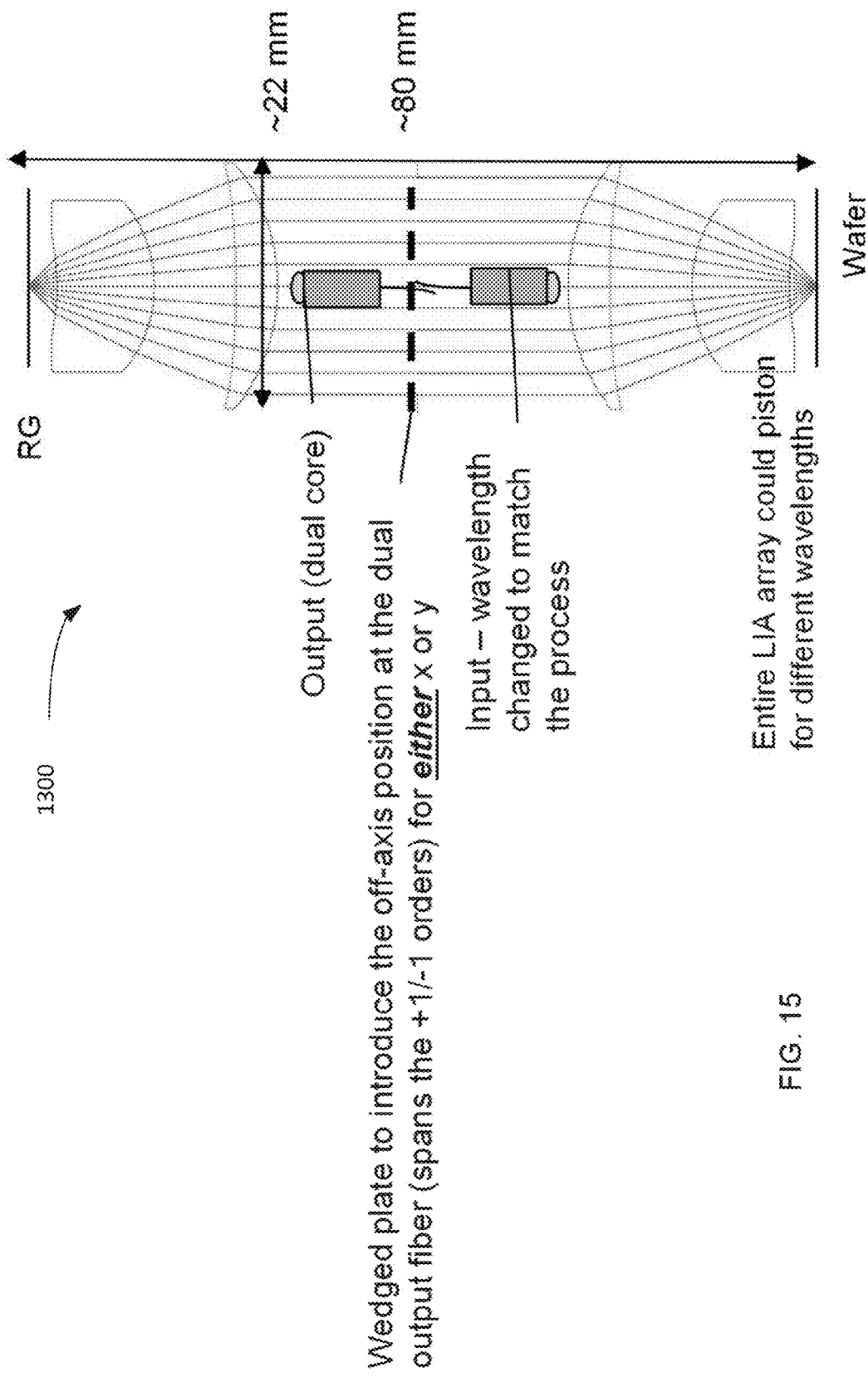
FIG. 15 is a schematic diagram of an embodiment of the lens system for use with embodiment of FIGS. 11A, 13A.
Figure 16:
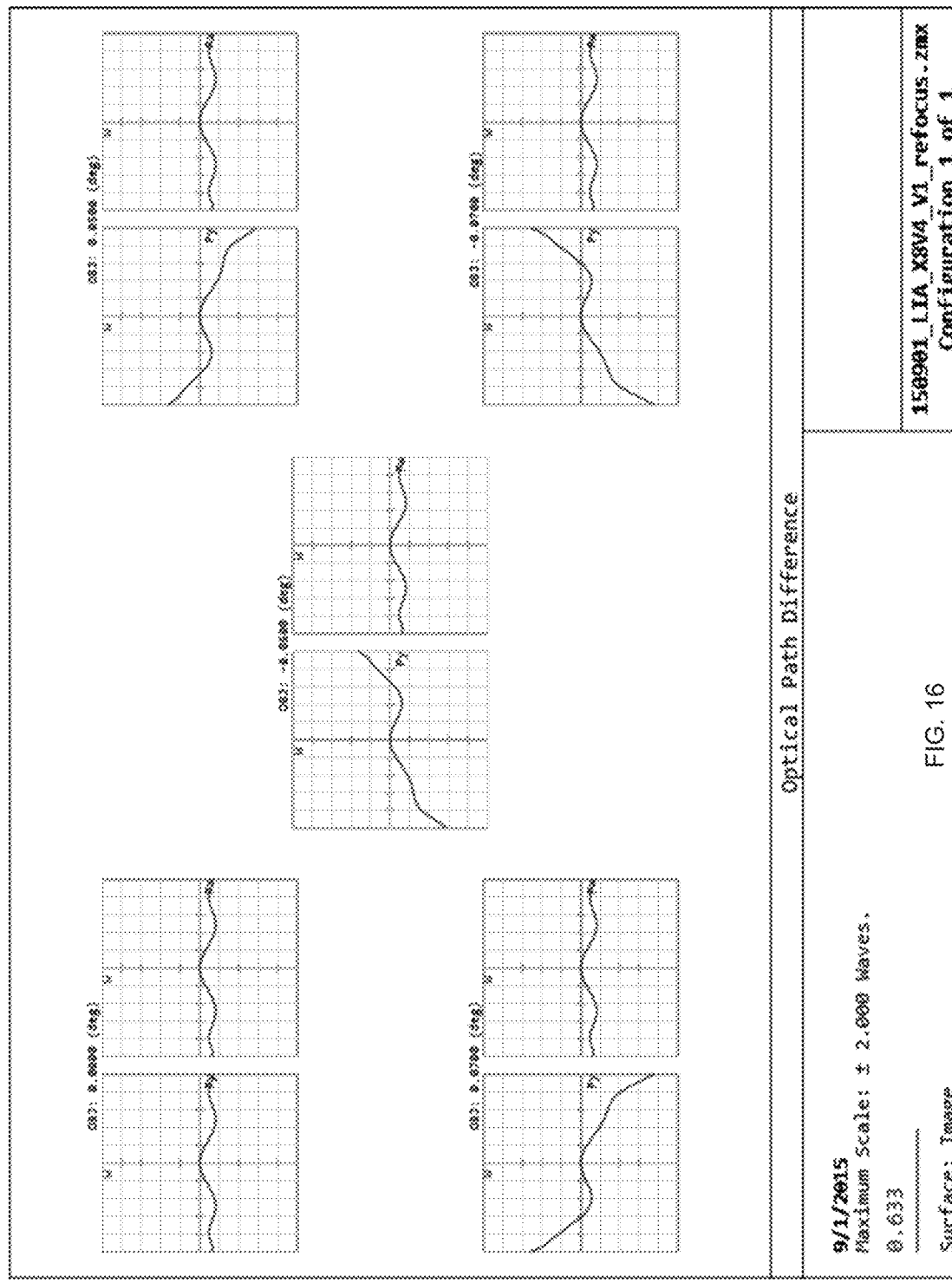
FIG. 16 includes plots illustrating optical path difference as a function of pupil coordinates for different angular fields, obtained with an optical design program used to design embodiments of FIGS. 14A, 14B.

Additional details of the proposed embodiments 1100, 1300 are summarized in reference to FIGS. 15 and 16.

In reference to FIG. 15, illustrating geometrical parameters of the embodiment(s), the combination of compound lenses 1110A, 1110B is symmetric about the plane containing the wedge 1130 (referred to as a pupil plane herein). For an optical fiber 1118A with NA of 0.1 (used in the input optic 1118 with a collimating lens 1118A having the focal length of about 15 mm), the distance between the lenses 1110A, 1110B can be at least 30 mm. The focal length of the lenslet 1126B of the output optic 1126 can be shorter than 15 mm, for example about 10 mm, while each of the output fibers 1126A can be a multimode output fiber (with NA that is typically 0.22), unlike the optical fiber of the input optic (which has to be an single mode fiber). This facilitates the outcoupling of light carrying the phase information from the sub-system 1100, 1300 towards the optical detector. The focal length of the LIA lens 1110A, 1110B is about 14 mm.

In the collimated space (between the lenses 1110A and 1110B, the wedge to change the tilt of one of the output beams advantageously doesn't cause any additional optical aberrations The 0th-order beam diffracted at the grating 1004 is diverging, and there are no concentric optical surfaces that can create parallel, coherent beams that will cause cyclic non-linear errors Having the single input beam on the MG insures that the 4 measurement beams are "incident" on the same wafer location, since they are actually all from the same, single, input beam.

FIG. 16 shows the optical path difference errors for different optical fields for the embodiment operating at 633 nm. The optical path difference (OPD) error of the proposed design is below 1 wave within the spectral range from 500 to 650 nm, if refocusing of the wafer plane is provided (either by moving the LIA assembly or the wafer stage—the wavelength used will be fixed for a given process. The working distance of the lens 1110A, 1110B exceeds 2 mm. In a related embodiment, the lens system is configured to be achromatic.

It has been verified that the sensitivity of the proposed system to the wafer tilt is operationally satisfactory. In particular, even for the wafer tilt over +/−1 mrad, the maximum angle difference between the beams diffracted at the grating 1004 is 0.2 arcseconds, which is too small to significantly reduce the contrast. The average angle varies +/−46 arcseconds (or about 0.225 mrad), which for the output lenslet 1126B with the focal length of about 10 mm results in 10 mm*0.000225 rad=2.25 micron of displacement at the output multi-mode fiber 1126A. Since the typical core size of the MMF is 50 microns, this will not prevent the output beams from being coupled to the output fiber.

Exposure Apparatus.

Figure 17:
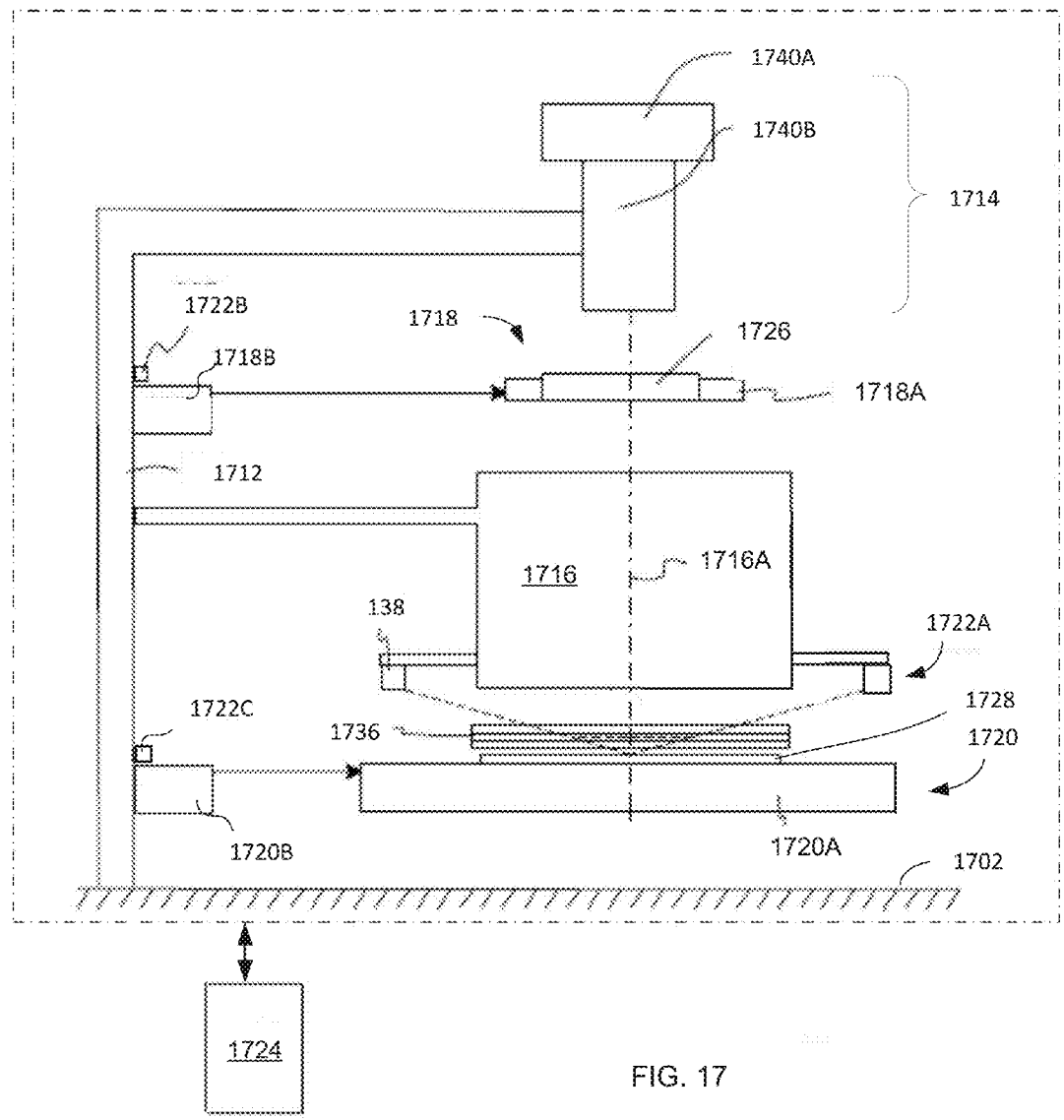
FIG. 17 illustrates an example of an exposure apparatus with which an embodiment can be used in practice.

An embodiment, in practice, is employed with or in association with an exposure apparatus. An example of an exposure apparatus (also interchangeably referred to as a lithographic apparatus, or lithographic exposure system, or exposure system), which may employ an embodiment of an autofocus system (AFS) for measurements of wafer displacements is provided, for example, in PCT/US2012/043186, U.S. Ser. No. 14/808,196, or U.S. Ser. No. 14/736,118, the disclosure of each of which is incorporated herein by reference. FIG. 17 schematically illustrates, in reference to the provided Cartesian system of coordinates, a schematic illustration of such exposure apparatus.

The exposure apparatus 1700 includes an apparatus frame 1712, an illumination system 1714 (also referred to as irradiation apparatus), an optical assembly 1716, a reticle stage assembly 1718, a wafer stage assembly 1720, a positioning system (shown as a combination of several units including systems 1722A, 1722B, 1722C), and a control system 1724. The design of the components of the exposure apparatus 100 can be varied to suit specific requirements. The exposure apparatus 1700 may be mounted to/on a mounting base 1702, such as the ground, a base, or floor, or some other supporting structure.

Apparatus Frame.

The apparatus frame 1712 is rigid and supports and/or houses at least the reticle stage assembly 1718, the optical assembly 1716, the wafer stage assembly 1720, and the illumination system 1714 above the mounting base 1702.

Illumination System.

The illumination system 1714 includes an illumination source 1740A and an illumination optical assembly 1740B. The illumination source 1740A emits radiation to which the wafer/work-piece 1728 is exposed and which is guided by the illumination optics of the assembly 1740B to the optical assembly 1716, along an optical axis 1716A. On its way to the optical assembly 1716, the beam of radiation illuminates a portion of the reticle 1726 to gain spatial pattern of irradiation representing the pattern of the reticle 1726.

The illumination source 1740A can be, for example, any of a g-line source (436 nm), an i-line source (365 nm), a KrF excimer laser (248 nm), an ArF excimer laser (193 nm), a F2 laser (157 nm), or an EUV source (13.5 nm). The wafer-illuminating (exposure) light may be provided at about 193 nm (by an ArF excimer laser system, for example) light (with a wavelength of 193 nm), but it can also include ultraviolet light such as described in, for example, U.S. Pat. No. 7,023,610. The source 1740A of illuminating light may exploit harmonic frequency conversion or utilize an optical-fiber based amplifier, to produce radiation at a predetermined wavelength. Alternatively, the illumination source 1740A can generate charged particle beams such as an x-ray or an electron beam. For instance, in the case where an electron beam is used, thermionic emission type lanthanum hexaboride (LaB6) or tantalum (Ta) can be used as a cathode for an electron gun. Furthermore, in the case where an electron beam is used, the structure could be such that either a mask is used or a pattern can be directly formed on a substrate without the use of a mask.

Optical Assembly.

The optical assembly 1716 projects and/or focuses the light passing through the reticle 1726 onto the work piece (wafer) 1728. Depending upon the design of the exposure apparatus 1700, the optical assembly 1716 can scale (i.e., to magnify or reduce, with a specific coefficient) dimensions of the pattern of the reticle 1726. In a specific implementation, the optical assembly 1726 may simply relay the pattern of the reticle 1726 onto the wafer (i.e., have a unit magnification).

Reticle Stage Assembly.

The reticle stage assembly 1718 holds and positions, (with the use of a reticle stage mover assembly 1718B) the reticle stage 1718A that retains the reticle 1726 relative to the optical assembly 1716 and the wafer 1728. The reticle stage mover assembly 1718B can be designed to move the reticle stage 118A along any of the x, y, z axes.

Wafer Stage Assembly.

The wafer stage assembly 1720 holds and positions (with the use of a wafer stage mover 1720B) the wafer 1728 with respect to the image of the illuminated portion of the reticle 1726 projected onto the wafer. The wafer stage mover 1720B can be designed to move the wafer 1728 along any of the x, y, z axis. In one embodiment, the wafer 1728 can be scanned while the wafer stage assembly 1720 moves the wafer 1728 along the y-axis.

Positioning System.

The positioning system (1722A, 1722B, 1722C) monitors movement of the reticle 1726 and the wafer 1728 relative to the optical assembly 1716 or some other reference. As shown in FIG. 17, the position system 1722 includes (i) an AFS 1722A that maps the topography of the wafer 1728 relative to the optical assembly 1716 along the Z axis (which is collinear with the optical axis 1716A), about the X axis, and about the Y axis prior to exposure of the wafer with improved accuracy; (ii) a reticle measurement system 1722B (only a portion of which is illustrated) that monitors the position of the reticle stage 1718A and the reticle 1726; and (iii) a wafer measurement system 1722C (only a portion of which is illustrated) that monitors the position of the wafer stage 1720A along the X and Y axes, and about the Z axis. Due to operation of the position system, the wafer stage assembly 1720 can be controlled to position the wafer 1728 with improved accuracy. The positioning system 1722 can utilize laser interferometers, encoders (such as those embodiments of which are discussed herein), autofocus systems, and/or other measuring devices.

One known implementation the autofocus system 1722A includes a reference system 1736 providing a reference signal used in conjunction with and related to the measurement of any changing operational parameter of the AFS 1722A but not the position of the wafer 1728 along the optical axis 1716A. The AFS 1722A further includes a measurement system 1738, which provides a measurement signal used in conjunction with and related to the measurement of anything changing in the AFS 1722A including (the change of, if present) position of the wafer 1728 along the optical axis 1716A. By comparing the reference and measurement signals, the position of the wafer 1728 is measured, which is accompanied with reduction of the stability requirements for many of the components of the AFS 1722A.

A typical measurement system 1738 may include an encoder assembly (not shown) that measures, in operation, the position of a work piece (as shown—the wafer 1728). For example, in some embodiments, the encoder assembly can be designed to monitor and/or measure the position of the work piece along two axes (e.g., along the x- and y-axes). Additionally and/or alternatively, the encoder assembly can be designed to measure and/or monitor the position of the work piece 1728 along all three axes (i.e., to specify the 3D position of the work piece 1728).

The conventional measurement system 1738 may also include a stage grating (not shown) that is secured to a side of the wafer stage 1720A (of the assembly 1720) that retains the work piece 1728, and one or more fixed encoder heads (not shown). The number of encoder heads and their mutual positioning and orientation can be varied according to the design of the exposure apparatus 1700 and/or the measurement system 1738, and the amount of travel of the stage 1720A along x- and y-axes. The use of multiple encoder heads enables the encoder assembly to more accurately measure the position of the stage 1720A, and thus the position of the work piece 1728 that is retained by the stage 1720A. Examples of the structure(s) of the measurement system 138 and encoder head(s) are discussed in detail in for example, U.S. 2014/0049762, which is incorporated herein by reference, and will not be addressed here additionally.

Control System.

The control system 17724 is operably connected to and governs the operation of at least the illumination system 1714, the reticle stage assembly 1718, the wafer stage assembly 1720, and the positioning system 1722. The control system 1724 acquires measurement data, from the positioning system 1722, that represent position and/or orientation and/or movement of the reticle 1726 and/or wafer 1728 with respect to the optical assembly 116 or another chosen reference. Based on these data, the control system 1724 controls the assemblies 1718, 1720 to precisely position the reticle 1726 and the wafer 1728. The control system 1724 can include one or more processors and electronic circuits, at least one of which may be specifically programmed to perform steps of data acquisition, data processing, and control of operation of the components of the apparatus 1700.

Generally, the exposure apparatus 1700 can be used as a scanning type photolithography system for optical transfer of a spatial pattern from the reticle 1726 onto the wafer 1728, with the reticle 1726 and the wafer 1728 moving synchronously. Alternatively, the exposure apparatus 1720 can be used as a step-and-repeat type photolithography system that exposes the reticle 1726 while the reticle 1726 and the wafer 1728 are stationary. The use of the exposure apparatus 1700, however, is not limited to a photolithography system for semiconductor manufacturing and can include, as a non-limiting example, the use as an LCD photolithography system that projects a liquid crystal display device pattern onto a rectangular glass plate or a photolithography system for manufacturing of a thin film magnetic head.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

Within this specification, embodiments have been described in a way that enables a clear and concise specification to be written, but it is intended and will be appreciated that embodiments may be variously combined or separated without parting from the scope of the invention. In particular, it will be appreciated that each of the features described herein is applicable to most if not all aspects of the invention.

In addition, when the present disclosure describes features of the invention with reference to corresponding drawings (in which like numbers represent the same or similar elements, wherever possible), the depicted structural elements are generally not to scale, for purposes of emphasis and understanding. It is to be understood that no single drawing is intended to support a complete description of all features of the invention. In other words, a given drawing is generally descriptive of only some, and not necessarily all, features of the invention. A given drawing and an associated portion of the disclosure containing a description referencing such drawing do not, generally, contain all elements of a particular view or all features that can be presented is this view, at least for purposes of simplifying the given drawing and discussion, and directing the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. The described single features, structures, or characteristics of the invention may be combined in any suitable manner in one or more further embodiments.

The invention as recited in claims appended to this disclosure is intended to be assessed in light of the disclosure as a whole, including features disclosed in prior art to which reference is made.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

Disclosed aspects, or portions of these aspects, may be combined in ways not listed above. Changes may be made without departing from the scope of the invention. In view of the numerous possible embodiments to which the principles of the disclosed invention may be applied, one should not view the implementation of the invention as being limited to the disclosed embodiment(s).

What is claimed is:

1. An optical sensor configured for operation with a lithographic exposure tool, the sensor comprising:
   an optical system including first and second lens systems disposed coaxially about an optical axis,
   an optical interface unit including first and second optical elements that are spatially separated from one another, disposed between the first and second lens systems, the optical interface unit configured
      to inject first light into the optical system at a first point located at the optical axis, and
      to extract second light from the optical system at a second point located at the optical axis,
   and
   an optical wedge positioned across the optical axis between the first and second lens systems and configured to spatially recombine different diffraction orders of at least one of the first and second lights, propagating through the optical system in operation of the optical sensor, regardless of spectral content of said at least one of the first and second lights.

2. An optical sensor according to claim 1, wherein, during said operation, the first light is delivered, by the optical system, from the first point to the first lens system along the optical axis and the second light is delivered, by the optical system, to the second point from the second lens system along the optical axis.

3. An optical sensor according to claim 1, wherein said optical wedge is positioned between the first point and the second optical system.

4. An optical sensor according to claim 1, wherein said optical wedge is positioned between the second point and the second lens system.

5. An optical sensor according to claim 1, wherein, during said operation, the second light is defined by a spatially-aligned combination of multiple beams of light that have diffracted on a component of the exposure tool upon propagating thereto through the first and second lens systems.

6. An optical sensor configured for operation with a lithographic exposure tool, the sensor comprising:
   an optical system including first and second lens systems disposed coaxially about an optical axis;
   an optical interface unit including
      a light input system disposed between the first and second lens systems to deliver first collimated beam of light towards the first lens system, and a light output system disposed between the first and second lens systems to receive a second collimated beam of light from the second lens system, the second collimated beam of light including light contained in the first collimated beam of light;
   and
      an optical wedge positioned across the optical axis between the first and second lens systems.

7. An optical sensor according to claim 6, wherein at least one of the light input and light output systems includes multiple optical fibers in optical communication with a lens of the at least one of the light input and light output systems.

8. An optical sensor according to claim 6, wherein the light input system is positioned to emanate light along the optical axis and the light output system is positioned to receive light along the optical axis.

9. An optical sensor according to claim 6, wherein the optical interface unit further comprises an optical reflector disposed across the optical axis to re-direct the first collimated beam of light before said first collimated beam of light is delivered to the first lens system and to receive the second collimated beam of light after it has been transmitted through the optical wedge and before said second collimated beam of light is delivered to the light output system.

10. An optical sensor according to claim 6, configured to be substantially operationally insensitive to a variation of an operational wavelength of the first collimated beam of light.

11. A mark-detecting apparatus configured to detect a mark formed on a mark region of an object, said apparatus comprising:
   a first optical system configured to supply a measurement beam of light;
   an objective optical system positioned to receive the measurement beam from the first optical system, to form a condensed measurement beam by condensing said measurement beam of light, and to eject the condensed measurement beam towards the mark region;
   a second optical system disposed to receive a positive-order diffraction beam of light and a negative-order diffraction beam of light through the objective optical system, the positive-order and negative-order diffraction beams of light having been generated at the mark region as a result of diffraction of the condensed measurement beam at the mark region, the second optical system configured to interfere said positive-order and negative order diffraction beams of light within the second optical system to form an interference beam of light; and
   an optical detector located to receive and detect said interference beam of light,
   wherein the second optical system is configured to co-directionally transmit the positive-order and negative-order diffraction beams regardless of whether there occurs a change of an angle of diffraction of the condensed measurement beam at the mark region;
   wherein the second optical system includes a reflector unit configured to reflect at least one of the positive-order and negative-order diffraction beams, incident on the reflector unit, an odd number of times,
   wherein the reflector unit includes a first light-reflecting member structured to reflect an even number of times, internally to the first light-reflecting member, one diffraction beam of light incident thereon through the objective optical system.

12. A mark-detecting apparatus according to claim 11, wherein the first optical system is configured to emit the measurement beam that contains light at a plurality of different wavelengths.

13. A mark-detecting apparatus according to claim 12, wherein said measurement beam that contains light at the plurality of different wavelengths including first light at a first wavelength and second light at a second wavelength, and
   wherein the reflector unit is configured to cause a spatial superimposition, of first portions of said positive-order and negative-order diffraction beams, wherein said first portions carry light at the first wavelength.

14. A mark-detecting apparatus according to claim 13, wherein the reflector unit is further configured to cause a spatial superimposition of second portions of said positive-order and negative-order diffraction beams, wherein said second portions carry light at the second wavelength.

15. A mark-detecting apparatus according to claim 13, wherein said positive-order and negative-order diffraction beams represent, respectively, a +1st order diffraction beam and a −1 order diffraction beam.

16. A mark detecting apparatus according to claim 11, wherein the reflector unit contains
   a beam-combining member disposed to receive a beam of light arriving thereto from the first light-reflecting member, to reflect said beam of light, and to transmit another diffraction beam of light arriving thereto through the objective optical system.

17. A mark detecting apparatus according to claim 16, wherein the detector is disposed in optical communication with said reflector unit to receive and detect light in a beam formed as a result of optical interference between said one diffraction beam of light and said another diffraction beam of light.

18. An optical sensor configured to detect a mark formed on an object, the optical sensor comprising:
   an optical system configured to supply a measurement light to the mark to generate a first diffracted light and a second diffracted light at the mark;
   a reflection member disposed to reflect at least one of the first diffracted light received from the optical system and the second diffracted light received from the optical system; and
   a detector configured to receive the at least one of the first diffracted light and the second diffracted light that has been reflected by the reflection member,
   wherein, in operation of the optical sensor, a difference between a first number and a second number is an odd number,
   the first number being a number of reflections of the first diffracted light by the reflection member and a second number being a number of reflections of the second diffracted light by the reflection member.

19. The optical sensor of claim 18, configured such that, when an orientational relationship between an optical axis of the optical system and the object changes from a first relationship to a second relationship,
   a positional relationship between a first optical path and a second optical path remains constant,
   wherein the first optical path is an optical path along which the first diffracted light propagates from the reflection member towards the detector, and
   wherein the second optical path is an optical path along which the second diffracted light propagated towards the detector.

20. The optical sensor of claim 18, wherein a number of reflection of the first diffracted light by the reflection member is zero, and a number of reflection of the second diffracted light by the reflection member is an odd number.

21. The optical sensor of claim 18, wherein the reflection member includes a plurality of reflecting surfaces, and wherein a first optical path and a second optical path are in the same plane,
   wherein the first optical path is an optical path of one of the at least one of the first diffracted light among the plurality of reflecting surface and the second diffracted light among the plurality of reflecting surfaces,
   wherein the second optical path is an optical path of another of the at least one of the first diffracted light among the plurality of reflecting surface and the second diffracted light among the plurality of reflecting surfaces.

22. The optical sensor of claim 18, wherein the reflection member includes an optical beam combiner configured to receive the first and second diffracted light spatially combine the first diffracted light and the second diffracted light to at least partially overlap the first and second optical paths upon propagation of the first and second diffracted lights therethrough.

23. The optical sensor of claim 18, wherein the reflection member includes a beam combiner configured to transmit the first diffracted light and to reflect the second diffracted light.

24. The optical sensor of claim 23, wherein the reflection member includes a first reflection element disposed to reflect the second diffracted light toward the beam combiner.

25. The optical sensor of claim 24, wherein the first reflection element includes an even number of reflecting surfaces that, in operation, interact with the second diffracted light.

26. The optical sensor of claim 25, wherein a first reflecting surface from the even numbers of reflecting surfaces is positioned to reflect the second diffracted light, that has arrived from the optical system, towards a second reflecting surface from the even numbers of reflecting surfaces.

27. The optical sensor of claim 26, wherein a first axis and a second axis cross each other,
wherein the first axis is an axis along which the second diffracted light impinges onto the first reflecting surface, from the even number of reflecting surfaces, and the second axis is an axis along which the second diffracted light is reflected by the second reflecting surface.

28. The optical sensor of claim 18, wherein the optical system is configured to cause the measurement light to impinge on the mark perpendicularly to the mark.

29. The optical sensor of claim 18, wherein a diffraction order corresponding to the first diffracted light is positive, while a diffraction order corresponding to the second diffracted light is negative.

30. The optical sensor of claim 18, wherein the first diffracted light represents a +1 diffraction order formed at said mark from the measurement light, and the second diffracted light represents a −1 diffraction order formed at said mark from the measurement light.

31. A mark detection apparatus configured to detect a position of a mark on an object, the mark detection apparatus comprising:
an optical system configured to supply a measurement light to the mark to generate a first diffracted light and a second diffracted light at the mark;
a reflection member disposed to reflect at least one of the first diffracted light received from the optical system and the second diffracted light received from the optical system; and
a detector configured to acquire the first and second diffracted lights from the reflection member,
wherein a difference between a first number and a second number is an odd number,
wherein the first number is a number of reflections of the first diffracted light by the reflection member and the second number is a number of reflections of the second diffracted light by the reflection member.

32. The mark detection apparatus of claim 31, configured such that, when an orientational relationship between an optical axis of the optical system and the object changes from a first relationship to a second relationship,
a positional relationship between a first optical path and a second optical path remains constant,
wherein the first optical path is an optical path along which the first diffracted light propagates from the reflection member towards the detector, and
wherein the second optical path is an optical path along which the second diffracted light propagated towards the detector.

33. The mark detection apparatus of claim 31, wherein a number of reflection of the first diffracted light by the reflection member is zero, and a number of reflection of the second diffracted light by the reflection member is an odd number.

34. The mark detection apparatus of claim 31, wherein the reflection member includes a plurality of reflecting surfaces, and wherein a first optical path and a second optical path are in the same plane,
wherein the first optical path is an optical path of one of the at least one of the first diffracted light among the plurality of reflecting surface and the second diffracted light among the plurality of reflecting surfaces,
wherein the second optical path is an optical path of another of the at least one of the first diffracted light among the plurality of reflecting surface and the second diffracted light among the plurality of reflecting surfaces.

35. The mark detection apparatus of claim 31, wherein the reflection member includes an optical beam combiner configured to receive the first and second diffracted light spatially combine the first diffracted light and the second diffracted light to at least partially overlap the first and second optical paths upon propagation of the first and second diffracted lights therethrough.

36. The mark detection apparatus of claim 31, wherein the reflection member includes a beam combiner which passes through the first diffracted light and which reflects the second diffracted light.

37. The mark detection apparatus of claim 36, wherein the reflection member includes a first reflection element disposed to reflect the second diffracted light toward the beam combiner.

38. The optical sensor of claim 37, wherein the first reflection element includes an even number of reflecting surfaces that, in operation, interact with the second diffracted light.

39. The optical sensor of claim 38, wherein a first reflecting surface from the even numbers of reflecting surfaces is positioned to reflect the second diffracted light, that has arrived from the optical system, towards a second reflecting surface from the even numbers of reflecting surfaces.

40. The optical sensor of claim 39, wherein a first axis and a second axis cross each other,
wherein the first axis is an axis along which the second diffracted light impinges onto the first reflecting surface, from the even number of reflecting surfaces, and the second axis is an axis along which the second diffracted light is reflected by the second reflecting surface.

41. The optical sensor of claim 31, wherein the optical system is configured to cause the measurement light to impinge on the mark perpendicularly to the mark.

42. The optical sensor of claim 31, wherein a diffraction order corresponding to the first diffracted light is positive, while a diffraction order corresponding to the second diffracted light is negative.

43. The optical sensor of claim 31, wherein the first diffracted light represents a +1 diffraction order formed at said mark from the measurement light, and the second diffracted light represents a −1 diffraction order formed at said mark from the measurement light.

44. A lithographic exposure apparatus configured to expose a target substrate as the object, comprising:
- the mark detection apparatus of claim 31;
- a substrate stage configured to hold the target substrate so as to change a position of the target substrate; and
- a controller configured to control a position of the target substrate based on, at least in part, by using an output from the mark detection apparatus, said output representing interaction between the first and second diffracted light.

45. An device manufacturing method comprising:
- exposing a circuit pattern on the target substrate with the use of the exposure apparatus of claim 44 to transfer the circuit pattern onto a surface of the target substrate;
- developing the substrate containing a transferred circuit pattern;
- forming a mask layer having a shape corresponding to the transferred circuit pattern; and
- processing the surface of the target substrate via the mask layer.

* * * * *